US 6,558,163 B2

(12) United States Patent
Riitano

(10) Patent No.: US 6,558,163 B2
(45) Date of Patent: *May 6, 2003

(54) ENDODONTIC SYSTEMS AND METHODS FOR PREPARING UPPER PORTIONS OF ROOT CANALS WITH INCREASINGLY RIGID FILES

(75) Inventor: Francesco Riitano, Soverato (IT)

(73) Assignee: Ultradent Products, Inc., South Jordan, UT (US)

( * ) Notice: Subject to any disclaimer, the term of this patent is extended or adjusted under 35 U.S.C. 154(b) by 26 days.

This patent is subject to a terminal disclaimer.

(21) Appl. No.: 09/848,073

(22) Filed: May 3, 2001

(65) Prior Publication Data

US 2001/0041324 A1 Nov. 15, 2001

Related U.S. Application Data

(63) Continuation-in-part of application No. 09/736,729, filed on Dec. 14, 2000, and a continuation-in-part of application No. 09/753,981, filed on Jan. 3, 2001, which is a continuation-in-part of application No. 09/536,821, filed on Mar. 27, 2000, which is a continuation-in-part of application No. 09/492,566, filed on Jan. 27, 2000, now Pat. No. 6,217,335, which is a continuation-in-part of application No. 09/325,035, filed on Jun. 3, 1999, now Pat. No. 6,059,572, which is a continuation-in-part of application No. 09/014,763, filed on Jan. 28, 1998, now Pat. No. 6,045,362, which is a continuation-in-part of application No. 08/885,906, filed on Jun. 30, 1997, now Pat. No. 5,775,904, which is a continuation of application No. 08/656,988, filed on Jun. 6, 1996, now Pat. No. 5,642,998.

(30) Foreign Application Priority Data

Jun. 6, 1995 (IT) ........................................ RM95A0377

(51) Int. Cl.[7] ................................................ A61C 5/02
(52) U.S. Cl. ..................................... 433/224; 433/102
(58) Field of Search ................................. 433/102, 224, 433/81

(56) References Cited

U.S. PATENT DOCUMENTS

| | | | |
|---|---|---|---|
| 322,265 A | 7/1885 | Donaldson | |
| 621,873 A | 3/1899 | Vajna | |
| 1,168,052 A | 1/1916 | Bolls | |
| 1,369,112 A | 2/1921 | Jones | |
| 3,715,331 A | 2/1973 | Molnar | 260/41 |
| 3,807,048 A | 4/1974 | Malmin | 32/40 R |
| 3,925,895 A | 12/1975 | Kliment et al. | 32/15 |
| 3,959,212 A | 5/1976 | Rockett et al. | 260/42.53 |
| 4,019,254 A | 4/1977 | Malmin | 32/57 |
| 4,190,958 A | 3/1980 | Martin et al. | 433/102 |
| 4,231,738 A | 11/1980 | Riitano et al. | 433/102 |
| 4,332,561 A | 6/1982 | McSpadden | 433/102 |
| 4,353,696 A | 10/1982 | Bridges | 433/125 |
| 4,364,730 A | 12/1982 | Axelsson | 433/141 |
| 4,466,795 A | 8/1984 | Plischka | 433/166 |
| 4,518,356 A | 5/1985 | Green | 433/102 |

(List continued on next page.)

FOREIGN PATENT DOCUMENTS

| | | |
|---|---|---|
| EP | 136500 | 4/1985 |
| FR | 2373269 | 7/1978 |
| FR | 2597327 | 10/1987 |
| GB | 2022475 | 12/1979 |
| IT | 1149157 | 12/1982 |
| IT | 1169326 | 7/1983 |

*Primary Examiner*—Kevin Shaver
*Assistant Examiner*—Melba Bumgarner
(74) *Attorney, Agent, or Firm*—Workman, Nydegger & Seeley

(57) ABSTRACT

A root canal is sequentially cleaned in sections from the crown to the apex by dividing it into three sections including an operative coronal portion, an operative middle portion and an apical portion. The pulp material is then sequentially removed from the portion of the root canal above the apical portion of the root canal with a set of instruments. The apical portion is then optionally cleaned with another set of instruments. Another optional set of instruments can also be used to improve the access into the apical portion such that irrigants can be delivered to the apical portion.

26 Claims, 8 Drawing Sheets

U.S. PATENT DOCUMENTS

| | | | |
|---|---|---|---|
| 4,571,183 A | 2/1986 | Nash | 433/116 |
| 4,681,541 A | 7/1987 | Snaper | 433/165 |
| 4,684,346 A | 8/1987 | Martin | 433/166 |
| 4,731,019 A | 3/1988 | Martin | 433/119 |
| 4,830,615 A | 5/1989 | Feinman et al. | 433/166 |
| 4,836,780 A | 6/1989 | Buchanan | 433/102 |
| 4,850,867 A | 7/1989 | Senia et al. | 433/102 |
| 4,886,843 A | 12/1989 | Walton | 522/174 |
| 4,889,487 A | 12/1989 | Lovaas | 433/102 |
| 4,895,146 A | 1/1990 | Draenert | 606/79 |
| 4,971,556 A | 11/1990 | Ritano | 433/102 |
| 4,984,985 A | 1/1991 | Edwardson | 433/123 |
| 4,992,048 A | 2/1991 | Goof | 433/102 |
| 5,017,138 A | 5/1991 | Schilder | 433/102 |
| 5,026,284 A | 6/1991 | Martin | 433/102 |
| 5,219,284 A | 6/1993 | Velvart et al. | 433/102 |
| 5,236,358 A | 8/1993 | Sieffert | 433/119 |
| 5,257,934 A | 11/1993 | Cossellu | 433/102 |
| 5,299,937 A | 4/1994 | Gow | 433/165 |
| 5,326,263 A | 7/1994 | Weissman | 433/224 |
| 5,498,158 A | 3/1996 | Wong | 433/102 |
| 5,503,554 A | 4/1996 | Schoeffel | 433/102 |
| 5,540,766 A | 7/1996 | Castellani | 106/35 |
| 5,605,460 A | 2/1997 | Heath et al. | 433/224 |
| 5,642,998 A | 7/1997 | Riitano | 433/224 |
| 5,658,145 A | 8/1997 | Maillefer et al. | 433/102 |
| 5,735,690 A | 4/1998 | Malentacca | 433/102 |
| 5,752,825 A | 5/1998 | Buchanan | 433/32 |
| 5,775,904 A | 7/1998 | Riitano | 433/102 |
| 5,868,570 A | 2/1999 | Hickok et al. | 433/102 |
| 6,042,375 A | 3/2000 | Riitano | 433/102 |

ENDODONTIC SYSTEMS AND METHODS FOR PREPARING UPPER PORTIONS OF ROOT CANALS WITH INCREASINGLY RIGID FILES

RELATED APPLICATIONS

This application is a continuation-in-part of U.S. patent application Ser. No. 09/736,729 entitled Endodontic Sealing Compositions and Methods for Using Such Compositions which was filed on Dec. 14, 2000. This application is also a continuation-in-part of U.S. patent application Ser. No. 09/753,981 entitled Endodontic System and Methods for the Anatonical, Sectional and Progressive Corono-Apical Preparation of Root Canals with Dedicated Stainless Steel Instruments and Dedicated Nickel/Titanium Instruments which was filed on Jan. 3, 2001. Ser. No. 09/753,981 is a continuation-in-part of U.S. patent application Ser. No. 09/536,821 entitled Endodontic Systems and Methods for the Anatomical, Sectional and Progressive Corono-Apical Preparation of Root Canals With Instruments Utilizing Stops which was filed on Mar. 27, 2000. Ser. No. 09/536,821 is a continuation-in-part of U.S. patent application Ser. No. 09/492,566 entitled Endodontic Systems and Methods for the Anatomical, Sectional and Progressive Corono-Apical Preparation of Root Canals with Minimal Apical Intrusion which was filed on Jan. 27, 2000 now U.S. Pat. No. 6,217,335. Ser. No. 09/492,566 is a continuation-in-part of U.S. patent application Ser. No. 09/325,035 which was filed on Jun. 3, 1999 and is entitled Endodontic Methods for the Anatomical, Sectional and Progressive Corono-Apical Preparation of Root Canals with Three Sets of Dedicated Instruments. Ser. No. 09/325,035 issued as U.S. Pat. No. 6,059,572. Ser. No. 09/325,035 was filed as a continuation-in-part of U.S. patent application Ser. No. 09/014,763 which was filed on Jan. 28, 1998 and is entitled Endodontic Methods for Progressively, Sectionally and Anatomically Preparing Root Canals with Specific Instruments for each Section having Predetermined Working Lengths. Serial No. 09/014,763 issued as U.S. Pat. No. 6,045,362. Ser. No. 09/014,763 is a continuation-in-part of U.S. patent application Ser. No. 08/885,906 which was filed on Jun. 30, 1997 and issued as U.S. Pat. No. 5,775,904. Ser. No. 08/885,906 is a continuation of U.S. patent application Ser. No. 08/656,988 which issued as U.S. Pat. No. 5,642,998. U.S. Pat. No. 5,775,904 and U.S. Pat. No. 5,642,998 are both entitled Endodontic Instrument for Rapid Mechanical Widening of the Canal Mouth and Specification of the First Two-Thirds. Priority of U.S. Pat. No. 5,642,998 is based on Italian Patent Application No. RM95A000377 which was filed on Jun. 6, 1995. For purposes of disclosure of the present invention, each of the foregoing applications is incorporated herein by specific reference.

BACKGROUND OF THE INVENTION

1. The Field of the Invention

The present invention is related to the field of endodontistry. More particularly, the invention is related to systems and operating methods for the preparation of root canals for obturation. The systems and methods involve the use of at least instruments which are dedicated for specific purposes in the inventive methods and systems and are designed for minimal intrusion into the apical portion.

2. The Relevant Technology

To preserve a tooth with a pulp that is diseased or is potentially diseased, it is generally necessary to remove as much of the pulp material as is possible from the pulp canal of the tooth, to shape the root canal(s) without excessively weakening the root canal walls, to prevent or minimize the presence of bacteria through the use of irrigants and dressings, and lastly, to clean the walls of the root canal(s) by removing the smear layer created during instrumentation of the root canal(s). These steps are all done to prepare the root cavity for sealing or obturation which involves filling the root canal with biocompatible materials, such as gutta percha, before the pulp cavity is sealed, thereby promoting the healing and functional recovery of the tooth. This procedure is referred to as root canal therapy.

As indicated hereinabove, root canal preparation involves pulp removal, cleaning of the root canal walls and shaping of the canal walls. This is typically achieved through a guided procedure with the use of instruments which are moved either manually, mechanically or by combinations thereof These instruments are files or bits that are configured to bore and/or cut. Mechanical instrumentation can be achieved through the use of endodontic handpieces coupled to instruments such as files. The endodontic handpieces can impart rotational motion to a file, reciprocal motion by alternately rotating a file clockwise and counterclockwise, sonic movements or ultrasonic movements.

With regard to operating procedures, there are two basic methods from which all of the canal-preparation techniques can be derived. These methods have been interpreted by various authors in an operational context and also in terms of the instrumentation. The primary conventional systems and methods for removing pulp material from the root canal of a tooth are the apico-coronal (step-back) technique and the corono-apical (crown-down) technique. Although these conventional cleaning techniques both rely generally on sequential increases in the diameter of instruments inserted into the root canal. The step-back technique involves the sequential use of instruments by first inserting an instrument all the way down to the apex of the root canal and then using progressively larger files to clean the root canal. So the step-back technique involves cleaning the root canal from the apex toward the crown. The crown-down technique uses a set of files that are inserted sequentially further and further into the root canal until reaching the apex and then instrumenting along the entire length of the root canal after the apex has been reached. Each technique has its own unique benefits and disadvantages.

In the step-back technique, each file that is sequentially used in the root canal has a larger tip diameter and a larger diameter at the top of the file. First, a series of instruments are inserted all the way to the apex that are increasingly larger until the apical portion is cleaned Then the remainder of the canal above the apical portion is cleaned and tapered by using a series of instruments that are successively larger and shorter. With each increase in diameter, the rigidity increases and the flexibility of the files decreases. As a result, it is not possible for the files to be moved in a manner that enables them to adjust to or to follow the contours of the perimeter surfaces of the root canal. This reduced flexibility also increases the likelihood that the files will fail to contact some portions while removing too much of the surrounding dentin in some areas through excessive abrasion and resulting in overthinning of the walls.

Not only is the completeness effected by the use of a set of files wherein each file is larger and more rigid than the preceding file but the ability to safely move the file within the canal is also limited. More particularly, the increasing rigidity results in decreased ability to negotiate the curves in the canal. Significant problems that can result from inserting increasingly rigid files and also from initially inserting a file all the way down to the apex includes laceration and transportation of the apical foramen, as well as misdirection and perforation of the wall.

The apex can be perforated by extrusion of the infected material through the apex due to the force exerted by the file on the material as the file is pushed downward to reach the apex. As a result, the periapical region can be invaded and contaminated. The potential for extruding infected material through the apical foramen of a necrotic tooth during the initial insertion of a file instrument all the way down to the apex is a particular disadvantage of the step-back technique. Another disadvantage is that the procedure has identical steps for working in either necrotic or vital root canals. In addition to exposing the tissue surrounding the tooth to the infected material, apical perforations may allow irrigants, filling or obturating material to flow out of the apex. Such apical perforations, as well as wall perforations, may delay tooth healing and may compromise the outcome of the therapy.

Perforations can also occur due to a failure to maintain a proper working length of the instrument during the procedure. As the canal is widened, curvatures are straightened thereby decreasing the required working length needed for the instrument to work. To properly determine the appropriate working length, many radiographs must be taken throughout the operation as the canal is continuously being modified, which alters the length. The time required to obtain the x-ray photographs or images and to adjust the working length of the instruments by repositioning the stops can result in a lengthy process. The step-back technique is also time intensive because a large number of instruments are required to complete the root canal therapy.

Another problem is the formation of ledges which can occur when a practitioner attempts to insert a file as far as the apex and the file is too inflexible to properly curve with the root canal or move around a protrusion. When a file is too inflexible to curve or flex as needed and is halted prematurely, the downward pressure exerted on the file, in conjunction with the tendency of the file to straighten itself, causes the tip of the file to dig into the side of the root canal and form a ledge. Such ledges are difficult to bypass; and if the ledge occurs very close to the apex, the ledge may give the practitioner the mistaken impression that the apex has been reached.

The crown-down technique was developed for several reasons. It was desired to shape the canal "conically" so as to keep the diameter of the foramen as straight as possible. The crown-down technique was also developed to prevent the discharge of septic material or obturation material from the apex after the initial canal-preparation step and to prevent subsequent vertical condensation due to the vertical pressure used to obturate the canals with heated gutta-percha. Additionally, the crown-down technique was intended to reduce the number of instruments utilized compared with the step-back technique. However, as discussed hereinbelow, significant potential problems may inherently result from use of the crown-down technique.

The crown-down technique generally involves the use of a set of file instruments that are incrementally inserted further and further into the root canal until reaching the apical portion. A file is first used that is sufficiently large that it binds near the top of the root canal. Then an incrementally smaller file is used so that it binds further down in the root canal. The files that are sequentially used may be incrementally longer or the files may have the same length and be further inserted into the root canal due to their increased narrowness. Once the root canal has been sequentially cleaned along its entire length down to the apex, then a file is inserted down to the apex that it capable of abrading against all of the surfaces of the root canal to eliminate the stepped configuration that has been created. Root canal cleaning procedures that are referred to as crown-down methodologies also often involve the use of a series of instruments after reaching the apex that extend to the apex and have an increasingly larger tapers to finish cleaning and shaping the root canal.

One example of the operational deficiency of the crown-down method lies in its association with instruments made of nickel/titanium Based on the greater flexibility of files formed from nickel/titanium compared with files formed from steel, proponents of the crown-down method in conjunction with nickel/titanium files assert that such files can better follow the curvatures of a root canal. Additionally, it has been asserted that such files are more likely to stay in the center of the root canal, thereby decreasing the likelihood of ledging or perforating the root canal walls. The ability of a nickel/titanium file to stay in the center is not necessarily desirable, in view of the morphology and perimetrical variety of root canals, and particularly the upper two-thirds of root canals which are typically laminar. In fact when rotation is imparted to an instrument that stays in the center of the canal, the file instrument works simultaneously and indiscriminately on all of the walls within reach of the file. Since root canal walls do not have equal thicknesses in all directions and at all different points along a root canal, some walls can be overthinned or perforated, while other walls remain untouched.

Moreover, because nickel/titanium files are more flexible than steel files, they tend to follow the path of least resistance and therefore cannot be used, in the same way as steel files, to be applied actively and intentionally by the operator. As a result, even when the operator knows the thickness of a particular portion, such as an interference or obstruction which the operator desires to rectify or straighten, the operator lacks the freedom to aggressively drive the file as needed and clean the portions that are difficult to reach. Accordingly, when a nickel/titanium file is used to clean a non-cylindrically shaped root canal, the file moves only at the center of the canal and/or the area of least resistance and fails to remove all of the necrotic tissue.

Some problems encountered in application of crown-down methodologies include overthinning of root canal walls, perforation of a root canal wall, excessively weakening of the walls of the tooth or a failure to fully contact all of the canal walls. These problems can be easily caused by the passive, self-guiding use of nickel/titanium files, particularly when utilizing instruments with progressively larger tapers in the transition from the first instrument to the next one in the set.

Overthinning can occur due to the indiscriminate thinning of the walls of the root canals by maintaining a file instrument in a central location during working rotation. Such overthinning can have devastating results. The inability to adequately direct a file used in accordance with the crown-down technique based on the practitioner's knowledge of the relative thicknesses of the portions of canal walls is a significant disadvantage of the technique.

Lateral perforation results from the formation of a borehole that increases in size until a hole is formed in the side of the root canal through the dentin and cementum around a root canal. Similarly, dangerous overthinning may occur when the borehole increases in size such that it extends into the cementum or very close to the cementum but has not yet created a hole in the side of the root canal then the root canal. Such lateral perforations and areas and that have been overthinned may be obscured from the x-ray due to concavities or curvatures in the root canal. As a result, the practitioner may not realize that the borehole has a formed a hole in the side of the root canal or extends into the cementum and may therefore mistakenly conclude that the root canal treatment has been successful. Infective bacteria that remained in the root canal, perhaps in the portions that were not contacted with the files, as well as toxins produced by the bacteria may then permeate through the cementum and cause infection or other complications.

An example of a cross-section of a laminar-type root canal cleaned by the crown-down technique which may result in successful root canal therapy since the instrumentation has not resulted in a perforation and the cementum has not been exposed is shown in FIG. 15D of U.S. Pat. No. 6,045,362. Although, problems such as perforations or overthinning have been avoided, FIG. 15D shows that large portions of the root canal remain untouched despite the change in morphology through the formation of large borehole. Note that the change in the morphology of the canal shown in FIG. 15D of U.S. Pat. No. 6,045,362 resulting from crown-down technique instrumentation occurs due to drilling in a passive, circular manner, especially when instruments are used having gradual and progressive tapers. The failure to contact significant portions of a root canal while forming a large borehole in a root canal is a very typical result of the crown-down technique since most root canals can be characterized as a laminar-type root canal.

It would be preferable to avoid the risk posed by failing to contact significant portions of the root canal. Since the practitioner is prevented from removing and essentially all pulp material, the practitioner cannot be assured of the reliability of the treatment. Additionally, the practitioner may not suspect that the working instruments have failed to contact every segment of the root canal since the canal has been instrumented from its top to its apex. Use of a set of files with increasingly greater tapers further contributes to a potentially incorrect conclusion that cleaning by such a conventional process has resulted in removing all material from the root canal. Further, the x-ray view of the tooth, as with the step-back technique, may give the incorrect impression that the root canal had been cleaned. It should also be remembered that while rotation of a set of passively actuated files, in the center of the canal, especially those with increasingly greater tapers, in accordance with the crown-down technique, may yield a configuration as shown in FIG. 15D of U.S. Pat. No. 6,045,362 and result in successful root canal therapy, there is a significant hazard of forming lateral perforations and overthinning due to the passivity of the instruments when linked to canal diameters and wall thicknesses that are still statistically unknown.

As in the configuration shown in FIG. 15D of U.S. Pat. No. 6,045,362, the configuration shown in FIG. 15E of U.S. Pat. No. 6,045,362 may also result in successful root canal therapy—but only for canals of the wholly tubular type. Although, the borehole does not extend through the dentin and into the cementum, the diameter of the preparation or borehole is nevertheless significantly larger than that of the original root canal was. The excessive thinning of the dental wall may result in significantly weaken the resistance of the walls to the stress of chewing, and may also cause a fracture of the root.

From the above discussion, it is clear that the actual morphology of the canals is not sufficiently considered when using the crown-down technique. More particularly, when files are used with successively larger tapers, each file, if actuated passively, is primarily limited to being rotated without substantial lateral movements guided by the operator. Since the majority of files are of the laminar type, this limitation poses a significant problem Without the ability to laterally move the files, it is not possible to make contact with every segment of the perimeter of the canal and some portions may receive too much contact.

In any event, if the files are rotated passively in a laminar canal or a canal which has a laminar-type anatomy for most of its upper portion, the result is a circular opening whose diameter corresponds to that of the file that was used. The file typically stays in the center of the canal during rotation, such that the tip of each file acts like a fulcrum and "ideally" stays in the same position as a rotation point. Since each successive file can move less laterally, each file simply makes a bigger borehole than the preceding file. Accordingly, the files cannot clean a root canal without significantly altering the original anatomy by leaving a footprint or borehole corresponding to the configuration of the instruments used. More specifically, the result is a footprint or borehole with a perimeter that corresponds to the perimeter of the biggest file that extends well beyond the original anatomy of the root canal and yet in most instances does not adequately clean significant portions of the root canal.

Although, the crown-down technique typically enables a practitioner to more efficiently clean a root canal than the step-back technique, they both require the practitioner to utilize many different instruments. The need to frequently change the cleaning instrument results in significant time requirements for cleaning a root canal. However, careful instrumentation in accordance with either tedious time consuming method does not avoid the problems set forth above in relation to apical perforation, wall perforation, overthinning or failure to clean all of the wall surfaces.

Based on the foregoing observations, methods and systems are needed in the endodontic arts which enable a dental practitioner to remove and clean essentially all pulp material in a root canal requiring root canal therapy.

It would also be an advancement in the endodontic arts to provide methods and systems that are based on the three-dimensional reality of teeth and do not relate solely to buccolingual x-ray views, thereby enabling a practitioner to remove and clean pulp material in a root canal without compromising the strength of the walls and the apical anatomy.

It would also be a beneficial development in the endodontic arts to provide methods and systems which encourage perimetrical contact of the instruments with the canal walls.

Additionally, it would be an advancement in the endodontic arts to provide methods and systems that enable a practitioner to remove and clean pulp material in a root canal in a manner that is less likely to result in failure due to bacterial contamination, overly thinning the root canal, perforations or due to infected material being pushed beyond the root from the coronal aspects of canals.

Finally, it would also constitute progress in the endodontic arts to provide methods and systems which yield a predictable success rate, minimal risk of breaking an instrument, lower costs, and an abbreviated operating time or an operating time that is at least as efficient as conventional techniques.

SUMMARY AND OBJECTS OF THE INVENTION

An object of the present invention is to provide, methods and systems which enable a dental practitioner to remove and clean essentially all pulp material in a root canal requiring root canal therapy by progressively cleaning sections of the root canal from the crown to the apex.

Another object of the present invention is to provide methods and systems developed based on the three-dimensional reality of teeth and not just buccolingual x-ray views, thereby enabling a practitioner to remove and clean pulp material in a root canal without compromising the strength of the walls and the apical anatomy.

An additional object of the present invention is to provide methods and systems which encourage perimetrical contact of the instruments with the canal walls.

Additionally, another object of the present invention is to provide methods and systems that enable a practitioner to remove and clean pulp material in a root canal in a manner that is less likely to result in failure due to bacterial contamination, overly thinning the root canal, perforations or due to infected material being pushed beyond the root from the coronal aspects of canals.

Finally, it is an object of the present invention to provide methods and systems which yield a predictable success rate, minimal risk of breaking an instrument, lower costs, and an abbreviated operating time or an operating time that is at least as efficient as conventional techniques.

Some of the features of the invention which enable these objects to be achieved are as summarized hereinbelow after explaining some unique terminology used in the application. Applicant utilizes a terminology based on the methodology disclosed herein. The term "operative root canal" refers to the pathway which starts at the occlusal surface of the tooth, continues with the cameral wall segment and the anatomical canal per se, and finally reaches the foramen. Of course, the anatomical root canal extends from the pulp chamber or the floor of the pulp chamber to the apex. The operative root canal is divided into three sections or portions which are referred to herein as "the operative coronal portion", "the operative middle portion" and "the apical portion". The operative coronal portion essentially includes the access cavity walls. The operative middle portion is the upper portion of the anatomical root canal while the apical portion is the lower portion of the anatomical root canal. A typical apical portion is the last or bottom 3 mm of the anatomical root canal.

The terms "operative coronal portion", "operative middle portion" and "apical portion" are unique terms that are distinct from the terminology conventionally utilized to refer to segments of a root canal. In the conventional crown-down method, the canal is customarily divided into the so-called "three thirds", including: the crown, the middle third, and the apical third. In reference to the conventional crown-down method, it is common to use the term "coronal third" to refer to the first part of the "anatomical" canal, originating at the floor of the pulp chamber or the upper limit of the middle third into which a tooth is customarily divided, with a theoretical line at the height of the neck.

During the root canal therapy, the pulp chamber can be opened to expose the anatomical root canal by any conventional method or instrument. Additionally, conventional methods and instruments can be used to prepare the operative coronal portion. However, unique methods and instruments are used in the operative middle portion while preferably simultaneously abrading the operative coronal portion. Additionally, after the operative middle portion has been cleaned, unique methods and instruments are used to improve access into the apical portion and to then clean the apical portion.

By envisioning the root canal as starting at the occlusal surface, practitioners can immediately identify any "interferences" or obstructions, as well as any protrusions of enamel, which may be disregarded. As a result, the instruments disclosed herein come into contact with every segment of the canal walls, including the obstructions, in order to achieve anatomical widening and also the rectification or straightening of the first two portions of the canal which include the operative coronal portion and the operative middle portion. This procedure opens the pathway for the preparation of the apical portion of the canal. The term "interference" refers to everything in the operative canal that hinders the rectilinear insertion of the instruments used, during the final cleaning phase of the procedure, preparation of the apical portion. The term "rectification" refers to the placement of the operative coronal portion or access cavity on the same axis as the operative middle portion. Rectification is achieved through the removal of interferences from the operative coronal portion and preferably from the operative middle portion of the operative canal as well.

The methodology disclosed herein involves the use of distinct instruments in the three portions of the anatomical root canal in different phases such that the root canal is cleaned progressively and sectionally. The instrument(s) associated with each phase have been designed specifically for that particular phase and accordingly have unique customized characteristics and features.

By cleaning the root canal in sections, the instruments can be adapted to the perimetrical or perimetral anatomy of the root canal. As a result, the entire perimeter or substantially all of the perimeter is contacted and cleaned along the length of the perimeter without substantially altering the configuration of the perimetrical anatomy. For example, a perimetrical anatomy that was primarily tubular or laminar will be enlarged but will still be primarily tubular or laminar. There will not be a large round borehole in the canal superimposed on the original perimetrical anatomy which corresponds to the diameter of the file that is used; as is the case with the nickel/titanium files used in crown down procedures that stay in the center of the canal even when the canal is laminar.

Additionally, the invention also enables the practitioner to prepare root canals in accordance with the anatomy of the root canal, even though the practitioner may not have been able to adequately identify the overall anatomy due to the inability to see the root canal as is the case from the mesial-distal view using standard radiography. Further, the invention also enables the practitioner to adapt to the contours of the root canal of all different types of teeth, by guiding instruments that have been designed to come into contact with every perimetrical segment of the walls.

Once the pulp chamber has been opened to expose the anatomical root canal, then the operative middle portion can be accessed. Before accessing the operative middle portion, however, it is necessary to determine the so-called "working length" of the first two portions of the operative root canal including the operative middle portion and the operative coronal portion. The methods for identifying the working length involve the use of x-rays or videography, performed with the aid of a centering device and through use of the long-cone method After the working length has been determined, then the proper instruments can be selected for use in the preparation of the operative middle portion.

The working length is determined by measuring the canal axis from the occlusal plane, in order to arrive at the apical limit of the root as indicated on the x-ray. A distance of 3 mm is deducted from the measured length. The result is the maximum working depth that the operative middle portion instrument(s) should reach. The foregoing calculations also figure in the predetermination of the working lengths for all other instruments utilized in the procedure. The instruments preferably are selected to have files with lengths that are equal to the working length; however, stops may also be used to ensure that the files have the desired working length.

In addition to the anatomical widening of the perimeter of the operative middle portion, the preparation of the first two portions also involves the removal of the interferences from the operative coronal portion and the operative middle portions, thereby allowing the rectification of the first two portions of the operative root canal. Please note that during preparation of the operative middle portion and rectification of the first two portions, any and all intrusion of the instrument(s) into the apical portion is avoided. The boundary between the operative middle portion and the apical portion has been estimated to be located between 3 mm and 5 mm from the end of the root canal, as shown on the x-ray. After preparation of the operative middle portion and rectification of the first two portions have been completed, the procedure moves to the third stage, in which the apical portion is prepared.

After the working length has been determined for the first two portions including the operative coronal portion and the operative middle portion, the operator selects an instrument from a set of instruments designed for use in the operative middle portion. Each instrument in the set of instruments comprises a handle connected to a file with an abrasive surface or in other words a shaft with tines or an abrading portion. Each file in the set has the same length which is selected such that the operative middle portion of the operative root canal is cleaned without significantly removing pulp material from the apical root portion. Additionally, each file is designed to have a taper that is larger than the taper of each preceding file. Each file or shaft has an abrading portion for abrading the surfaces or walls of the root canal. In contrast to conventional files, as set forth in greater detail hereinbelow, the abrading portion may extend along the entire length of the file to enable the instrument to be used to clean the operative middle portion while also abrading the operative coronal portion.

The files of the instruments in the first set are preferably formed from stainless steel to enable the file to be moved in the desired manner. The files of the instruments in the first set are designed such that each file has sufficient flexibility to be flexed or curved to urge the abrading portion against the surfaces of the root canal and sufficient rigidity to apply pressure against the surfaces of the root canal as the abrading portion of the file is urged against the surfaces of the root canal and simultaneously moved in a cleaning motion. Additionally, the files have adequate resilience to avoid being substantially deformed as the file is flexed or curved to urge the file, particularly the abrading portion, against the surfaces of the root canal.

The contours of the perimeter of the root canal in the operative middle portion are followed as the file of the instrument(s) is flexed or curved against the surfaces of the root canal and simultaneously moved in a cleaning motion. Since the contours are followed, the perimeter is widened and smoothed but the original shape is not substantially altered.

After the operative middle portion has been cleaned, the apical portion may be cleaned by several different techniques or combinations thereof. One method involves no abrasive instrumentation within the apical portion just insertion of appropriate irrigation instruments. Since removal of the pulp material from the operative middle portion removes the majority of bacteria in the pulp canal, it has been found that it may not be necessary to abrade the apical portion.

Irrigants are delivered into the apical portion to maintain the debris derived from cleaning the root canal in suspension. The debris is then removed as the particles of the smear layer yielded from the action of the files used to prepare the canal may result in clogging the apical portion of the root canal with a plug. After the debris has been removed, the proper preparation and filling of the apical portion of the root canal can be achieved.

By eliminating or minimizing abrasive instrumentation within the apical portion, the potential for complications is diminished. As discussed above in the Background, most errors in performing root canals occur during instrumentation of the apical portion of the root canal. The apical portion is the most delicate part of the root canal and it is the most distally located Accordingly, it is highly advantageous to just irrigate and then remove the irrigant and debris, since many complications occur during abrasive instrumentation.

However, in some instances, it may be necessary to improve access into the apical portion such that an irrigation needle can be deployed to deliver irrigants to the apical portion. Access into the apical portion is improved by widening, for example, at least the entrance of the apical portion or the entire apical portion.

Alternatively, another method involves the use of a set of instruments designed for cleaning the apical portion in an abrasive manner. Such a method may be initiated directly after the operative middle portion of the operative root canal has been cleaned. However, it may be necessary to have two phases of instrumentation within the apical portion of the operative root canal including widening and abrasive cleaning of the apical portion. More particularly, it may be necessary to improve the access into the apical portion before performing the abrasive instrumentation by widening the transition between the operative middle portion and the apical portion to enable irrigants to be delivered into the apical portion.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings listed hereinbelow.

DETAILED DESCRIPTION OF THE PREFERRED EMBODIMENTS

Figure 1:
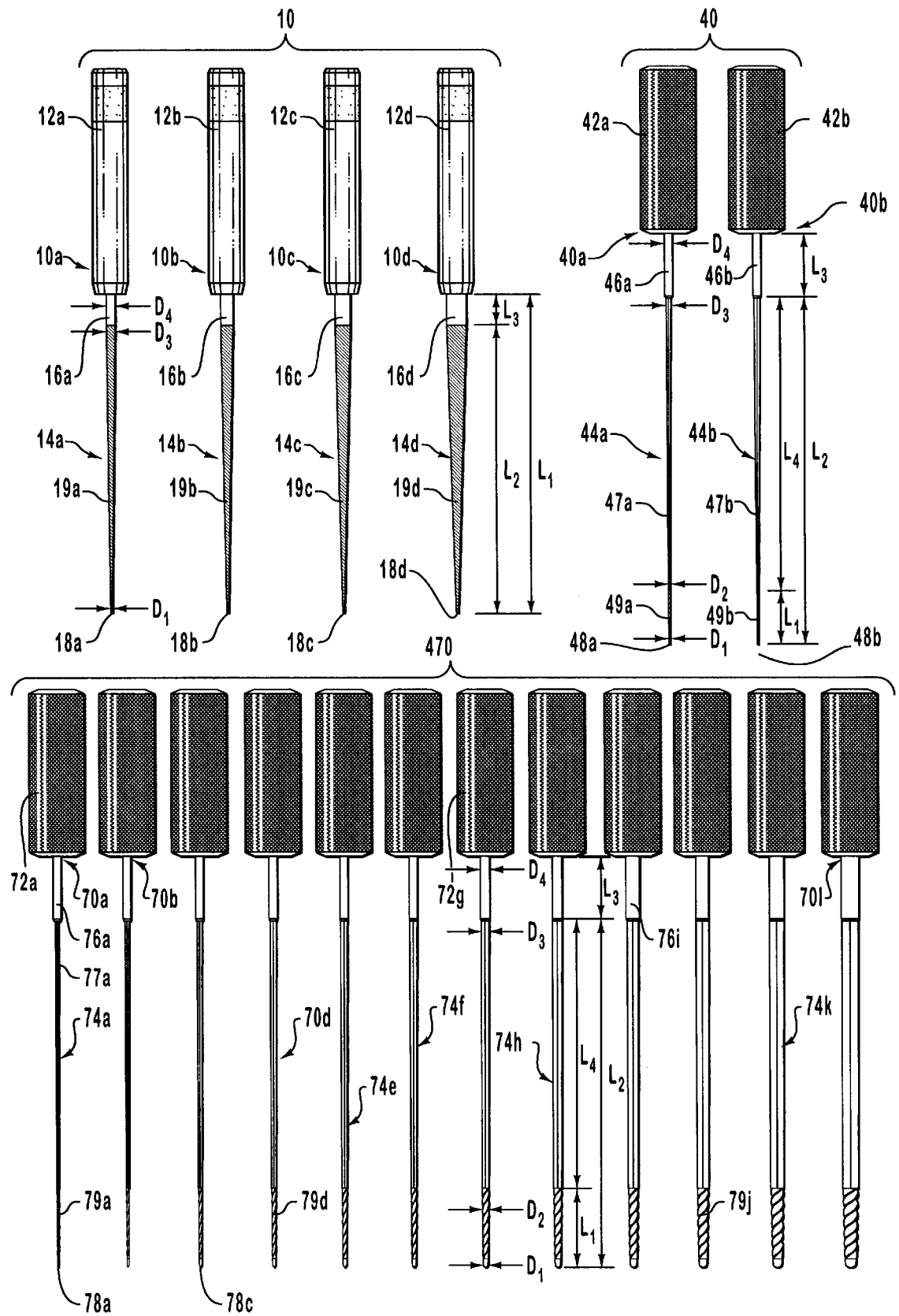
FIG. 1 is a view of a system of endodontic tools including a first set of instruments for cleaning the operative middle portion of an operative root canal, a second set of instruments for improving the access into the apical root portion and a third set of instruments for cleaning the apical root portion.

The present invention relates to systems and methods for cleaning root canals through the removal of pulp material from the root canals. The invention provides for cleaning the root canal in progressive sections from crown to apex. FIG. 1 depicts a system of instruments that includes three distinct sets. After the pulp chamber is opened and preferably after further preparations, instruments from a first set of instruments such as set 10 are sequentially introduced into the root canal to clean the root canal up to the apical root portion or in some instances a single instrument is used. The apical portion is preferably cleaned by delivering an irrigant into the apical portion and then removing the irrigant along with any debris. In some instances, an additional instrument or set of instruments may be optionally introduced to improve the access into the apical portion for introduction of a cannula of an irrigation tip such as set 40. Alternatively, the apical root portion may also be cleaned with another instrument or set of instruments such as set 70.

The invention enables a dental practitioner to remove and clean essentially all the pulp material in a root canal requiring root canal therapy. The cleaning is achieved in a manner that is safer in terms of over thinning of the root canal and perforations and yet requires less instrumentation than conventional techniques.

Figure 2A:
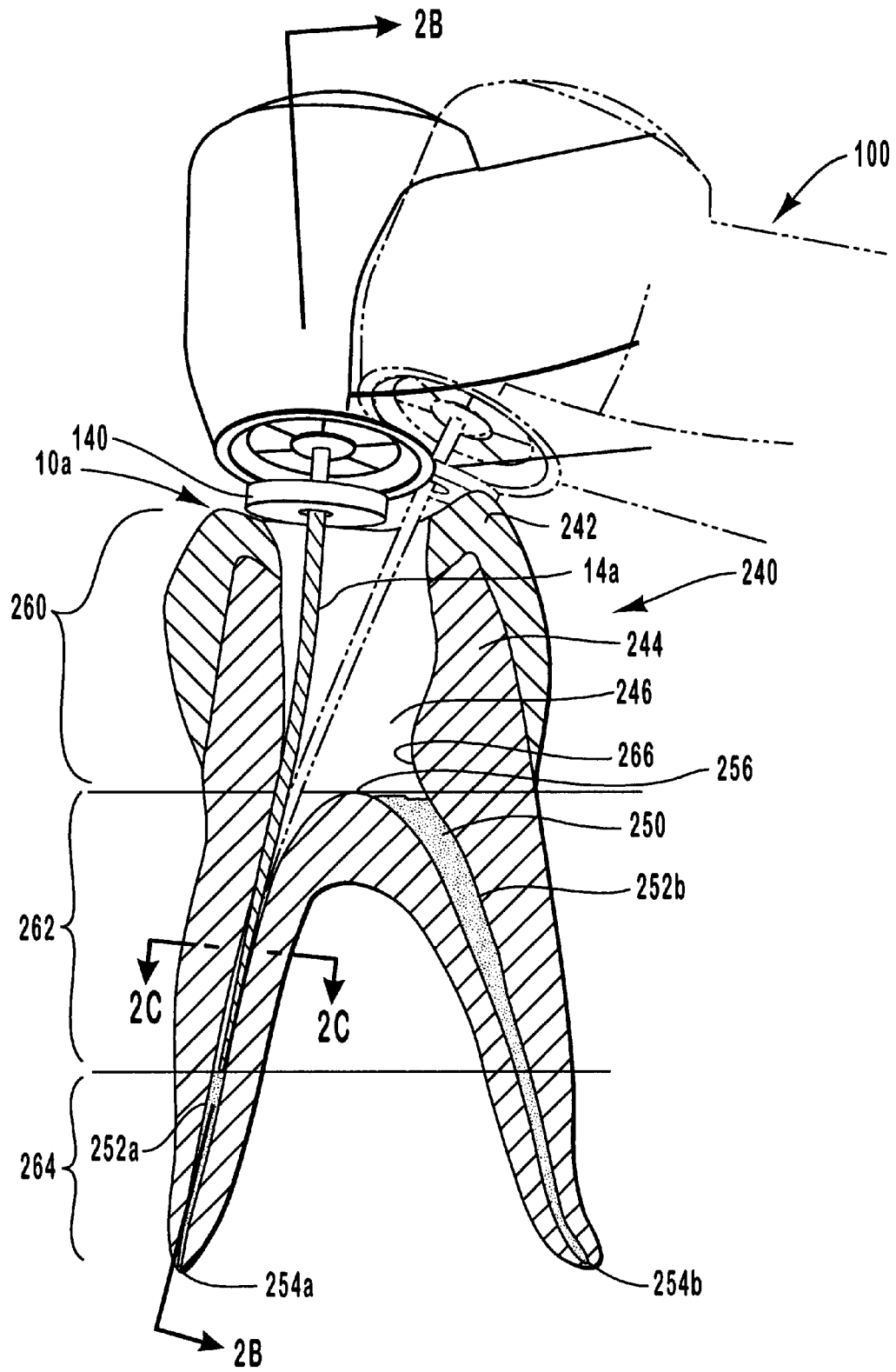
FIGS. 2A–2B show embodiments of endodontic files operated by a driver, such as an electric motor or an air turbine, with lengths that enable the portions of the root canal above the apical portion to be cleaned.
Figure 2B:
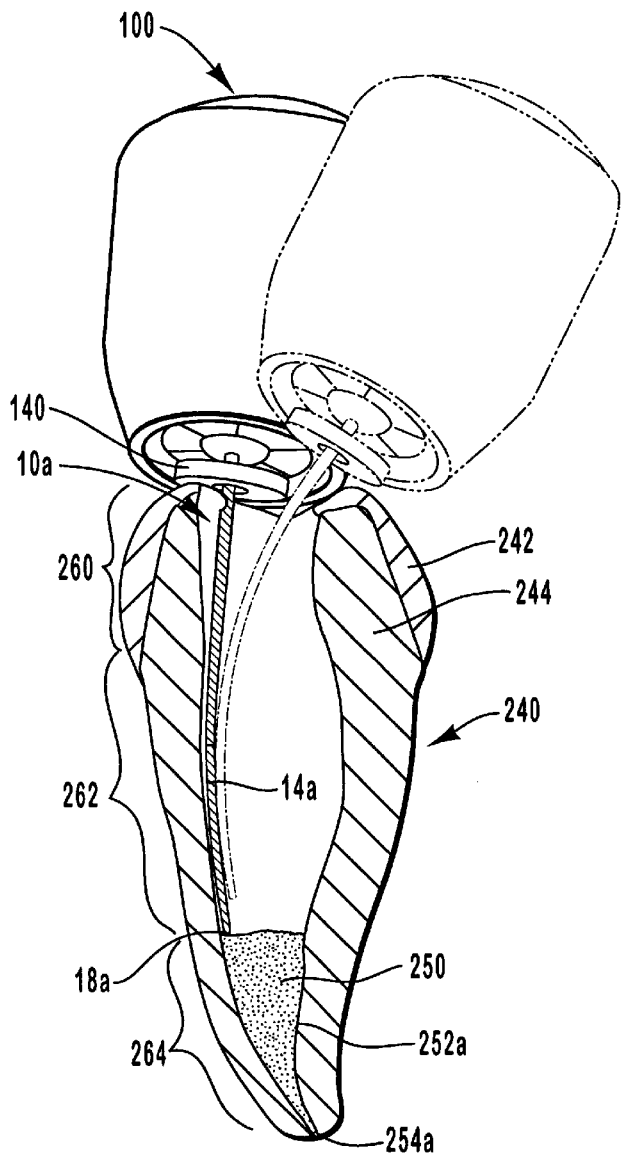
Figure 2C:
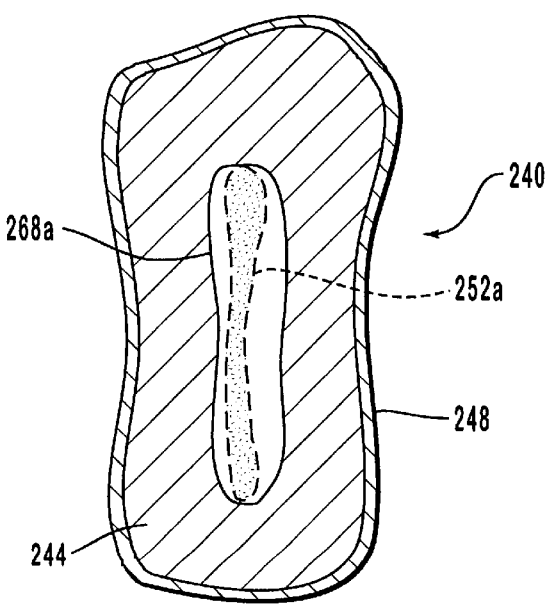
FIG. 2C is an enlarged transverse cross-sectional view of the tooth shown in FIG. 2A taken along cutting line 2C—2C to show that the anatomy of the root canal has not been substantially altered by the cleaning thereof and to show the shaping of the canal in preparation of filling the root canal.
Figure 3:
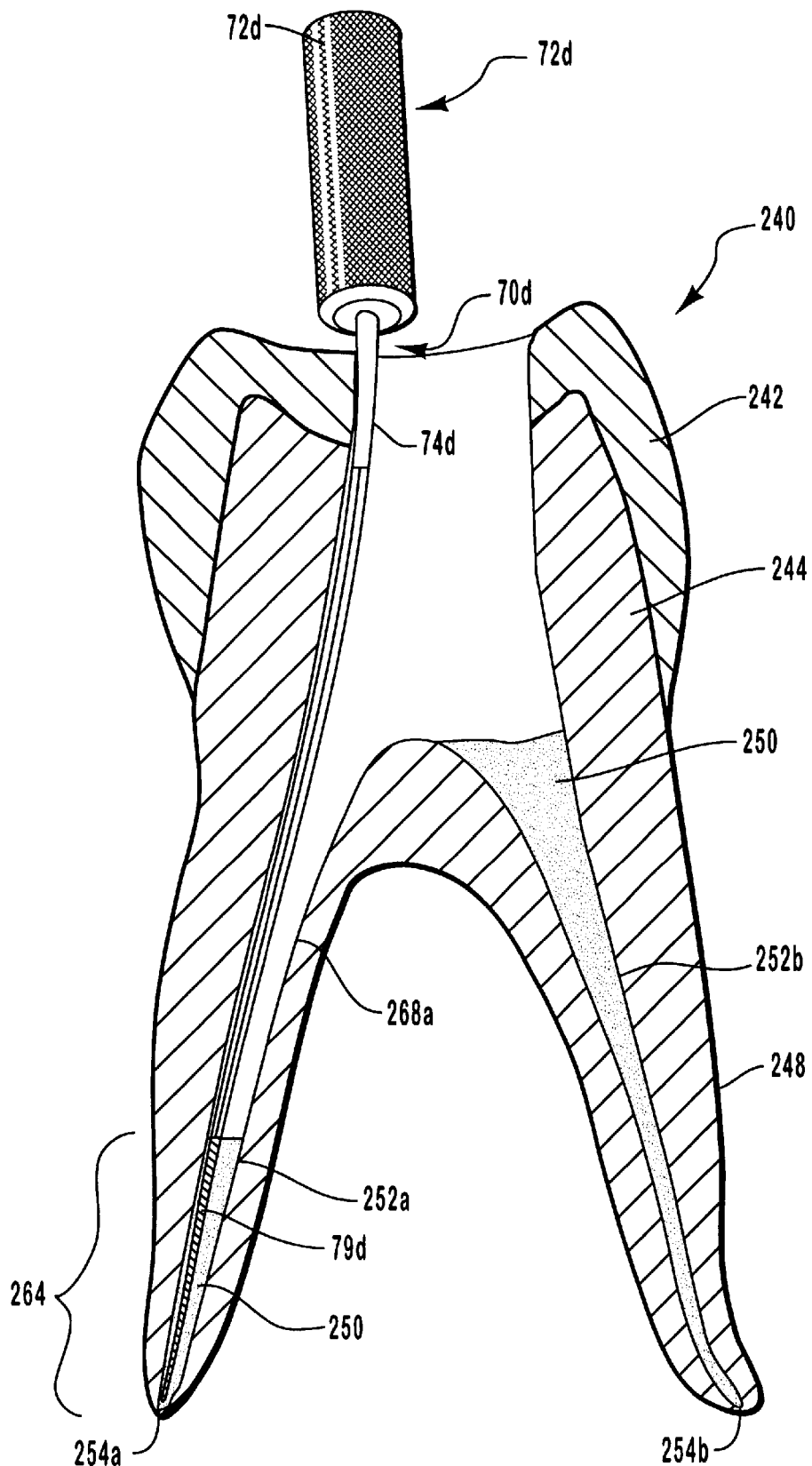
FIG. 3 is a longitudinal cross-sectional view of a tooth with a file inserted into a root canal having a length that is sufficient to reach the apex.

To appreciate the nomenclature used for these sets, reference is made to FIGS. 2A–2B and 3 which depict a molar 240 in various stages of the root canal cleaning procedure. The sections of the operative root canal being cleaned in FIGS. 2A–2B include the operative coronal portion 260 and the operative middle portion 262. The remainder of the operative root canal, the apical portion 264 is shown being cleaned in FIG. 3. The operative coronal portion 260 essentially includes the access cavity walls down to the floor 256 of pulp chamber 246. The operative middle portion 262 is the upper portion of the anatomical root canal while the apical portion 263 is the lower portion of the anatomical root canal. A typical apical portion 264 is the last or bottom 3 mm or 4 mm of the anatomical root canal. Stated otherwise, the apical portion of the root canals shown in FIGS. 2A–3 is the 3 mm to 4 mm above apices 254a and 254b. However, the actual length of the apical portion varies depending on many factors such as the type of tooth and the age of the tooth.

The divisions of the operative root canal are distinguished from the nomenclature of the anatomical root canal as used to designate the sections before opening the tooth wherein the anatomical root canal is divided into the apical portion and the coronal portion. The coronal portion of the anatomical root portion is conventionally defined as the upper portion of the anatomical root canal which terminates at the floor of the pulp chamber. However, once the pulp chamber is exposed and instruments are introduced into the root canal, the opening into the tooth should be treated as an extension of the operative root canal as it is then a continuous chamber or open tract. Accordingly, the access walls are considered part of the operative root canal and are designated as the operative coronal portion 260. In reference to the anatomical root canal 252a, the operative middle portion 262 is defined as extending from floor 256 down to an area of anatomical root canal 252a, such that the length of the operative middle portion is the top two-thirds of anatomical root canal 252a.

As previously indicated, the three sections are treated in primarily distinct sequential phases including: preparation of the operative coronal portion, then cleaning or preparation of the operative middle portion, optionally improving access to the apical root portion and finally cleaning of the apical portion preferably by just irrigating the apical portion or alternatively by use of abrasive instrumentation.

Before the sets of instruments in the system shown in FIG. 1 are utilized, it is first necessary to expose the pulp chamber by removing the top of the chamber. This can be achieved, for example, through the use of an instrument such as an instrument with a bur, which is preferably a diamond bur used in conjunction with a low or high speed handpiece. However, any suitable instrument can be utilized such as those disclosed in Italian Patent No. 1,142,983 or Italian Patent No. 1,149,157, which are hereby incorporated by reference. This first phase in the procedure also preferably involves other steps to enhance accessibility into operative middle portion 262 and also apical portion 264.

After the pulp chamber has been exposed during the first phase, it is preferable to remove or reduce dentinal or enamel protrusion or irregularities that may obscure or hinder access of instruments into the remaining portions of the operative root canal during the subsequent phases. FIG. 2A shows a dentinal shelf 266 above root canal 252b while the overhanging portions of enamel 242 and dentin 244 have been removed on the other side above root canal 252a in preparation for removing pulp material 250 from root canal 252a. Interferences are preferably removed or minimized such that instruments can be inserted in the anatomical root canal in a relatively straight manner. Rectification or regularization can be achieved by any suitable means. An example of a means for rectifying dentinal shelves is set forth in U.S. Pat. No. 5,642,998 and in U.S. Pat. No. 5,775,904 which were incorporated by reference hereinabove. It may also be necessary to widen the tract of the operative coronal root canal. Some dentists may prefer to obtain greater access through a cuspidectomy. Note that during the root canal procedure, a rubber dam is typically used to isolate the tooth, which may require in some instances, the rebuilding of the pulp chamber walls. During this phase as well as the others, it is generally necessary to irrigate the root is canal with irrigants or a root canal conditioner/lubricant.

Once the operative coronal portion has been properly prepared, then the three sets of instruments shown in FIG. 1 can be used. These three distinct set of instruments are each specifically referred to as: a set of instruments for cleaning the operative middle portion, identified as operative middle portion set 10; an optional set of instruments used to improve access into the apical root portion, identified as optional set 40; and a set of instruments for removing and cleaning essentially all pulp material from the apical root portion, identified as apical portion set 70. File 14*a* of instrument 10*a* from operative middle portion set 10 is shown being used in FIGS. 2A–2B to clean to clean the pulp material 250 from the root canal operative middle portion 262 of root canal 252*a*. Once operative middle portion 262 has been cleaned, then the apical portion 264 is cleaned as shown in FIG. 3 with one of the instruments from apical portion set 70 such as 70*d*. In some instances, it is necessary to use an instrument from optional set 40 before cleaning the apical portion in order to widen the transition from the operative middle portion 262 to apical portion 264.

The sequential use of each set and features of the instruments are discussed below, specific details of an exemplary embodiment of a system of sets is provided below in detail in Example 1 of the Examples of the Preferred Embodiment. It should be understood, however, that each instrument has a file with a top end extending from a handle. File instruments can also be manufactured that are just a file without a handle.

After the operative coronal portion has been adequately prepared, the overall length of the root canal is identified, typically by use of radiography, in order to determine the preferred working length for the instrument or set of instruments to be used. Once the overall length of the root canal has been identified, then the combined length of operative middle portion 262 and the operative coronal portion 260 are determined by subtracting about 3 mm to about 4 mm from the overall length. Determination of the combined length of operative middle portion 262 and the operative coronal portion 260 enables the practitioner to select a set such as set 10 with instruments having files with lengths that are appropriate for cleaning or preparation of operative middle portion 262. The total radiographic length is preferably derived from a radiograph made using a localizator and a long cone radiographic head.

Once an instrument or a set of instruments have been selected that have an appropriate length then the next phase in the procedure can proceed as shown in FIG. 2A. While the primary objective in this phase is cleaning or preparation of operative middle portion 262, it may also involve to some extent further rectification of the operative coronal or access portion 260 through further removal of any ledges or outcroppings which prevent straight and easy access into the operative middle portion 262. Additionally, it may also involve some degree of rectification of the upper region or segment of operative middle portion 262.

As shown in FIG. 2A, a file such as file 14*a* of file instrument 10*a* is inserted into root canal 252, down through operative middle portion 262 without extending substantially into apical portion 264. After file instrument 10*a* is used, then the other three instruments 10*b–d* are sequentially used to further clean and shape operative middle portion 262 and operative coronal portion 260.

File instrument 10*a* has a file 14*a* extending from handle 12*a*. File 14*a* has a shank portion 16*a* and tines or an abrading portion 19*a*. The abrading portion extends from tip 18*a* to shank portion 16*a* at the top end of file 14*a*. The features of the other files are similarly numbered.

By properly selecting a combination of factors including the diameters of the files at the top ends and at the tips as well as the material used to form the files, the files are designed such that each file has sufficient flexibility to be flexed or curved to urge the abrading portion against the surfaces or walls of the root canal and sufficient rigidity to apply pressure against the surfaces of the root canal as the abrading portion of the file is urged against the surfaces of the root canal and simultaneously moved in a cleaning motion. Additionally, the files have adequate resilience to avoid being substantially deformed as the file instrument is flexed or curved to urge the abrading portion against the surfaces of the root canal.

As shown in FIG. 1, the diameter of the top end of each abrading portion is incrementally larger when comparing files 14*a–d*. Accordingly, the diameter of the top end of each successive file introduced into the operative middle portion is greater than the diameter of the top end of each preceding file.

The diameter of each tip 18 in a set of instruments is essentially the same such that the diameter of tip 18*a* is about the same as the diameter of tips 18*b–d*. For example, a set of instruments may all have tip diameters of about 0.10 mm. A set may also be designed such that the instrument intended to be inserted first has a tip diameter of about 0.10 mm while the other instruments in the set have a tip diameter of about 0.13 mm. A set with slightly different tip diameters, such as a set of three or four instruments with respective tip diameters of 0.10 mm, 0.10 mm, 0.13 mm and 0.13 mm, and in any event not exceeding 0.15 mm, is still considered to have substantially constant tip diameters within the set as the difference in size is very minor and the diameters do not sequentially increase for each instrument. In an alternative embodiment, the tip diameter may vary between instruments in a set such that, for example, the tip diameter of each sequentially inserted file is progressively larger. The tip may be generally sharp and configured for at least minimal cutting capability. The tip may also be more rounded such that the tip has essentially no cutting capability.

Since the tip diameters are essentially equal and since the diameter of the top end of each successive file introduced into the operative middle portion is larger than the diameter of the top end of the preceding file, the taper of the abrading portion of each successive file in the set is larger than the abrading portion of the preceding file. For example, the taper may range from 0.02 to 0.13 and increase in increments for each successive file. Each successive file accordingly has an increased surface area for cleaning the root canal. Additionally, as files are inserted into a root canal with larger and larger tapers, the rigidity of the upper half of each successive file also increases or more particularly, the rigidity of the upper half of each successive abrading portion increases. The increase in rigidity in the upper half enables the practitioner to more easily remove interferences and to properly rectify the operative coronal portion 260 and the operative middle portion 262. The sequential use of files in a set wherein each file has greater rigidity than the previously introduced file along at least an upper part of the abrading portion of each file enables each sequentially introduced file to more rapidly and aggressively clean than the previously introduced file. The cleaning is more rapid and aggressive as at least the top end of each abrading portion of each sequentially introduced file applies greater force against the root canal surfaces than the previously introduced file. Accordingly, the contours can be gently followed by the instrument or instruments initially used and then the contours of the root canal can be followed by the subsequently used instruments as the root canal is more aggressively shaped. Note that the rigidity does not increase in a manner that prevents even the final instrument used in the cleaning of the operative middle portion and the operative coronal portion from following the contours of the root canal.

When the tip diameter remains essentially the same for the instruments in the set and the taper is increasingly larger for the abrading portion of each sequentially used instrument the top end of each abrading portion is more rigid for each sequentially used instrument, however, the rigidity at the tip is about the same. Stated otherwise, the difference in rigidity between the abrading portions of the files diminishes from the top end of each abrading portion to the tip. While there may be some comparative increase in rigidity at the lower region of each sequentially utilized abrading portion, the increase in rigidity is not as pronounced or is sufficiently nominal to have little effect when compared with the increase at the top end of each abrading portion. Note that the flexibility of the lower portion, particularly within the region closest to the tip, also remains essentially constant. In other embodiments, the taper of the abrading portions may be constant and have increasing rigidity along the entire length when compared to the previously inserted file by designing the files with larger top ends and larger tip diameters.

The consistency in rigidity and flexibility at the lower region or half is useful since the lateral perimetrical force applied to the handle is primarily transferred to its upper half or at least the part closest to the handle, which is the strongest part of the file. So as the upper part of the abrading portion is aggressively urged against root canal surfaces, the force applied by the lower part of the abrading portion is not significantly different. This is beneficial since root canals taper in diameter. Additionally, a root canal that is laminar at the top of an operative middle portion often tapers to a configuration that is primarily round. In such instances, the tip of the file rotates in a round root canal segment while the top end of the abrading portion is pushed around the laminar perimeter of the top of the operative middle portion The file can be formed from any suitable material. In forming a file, the material is preferably selected in view of the dimensions and design, to yield a file having the desired properties with respect to flexibility, resilience and/or rigidity as set forth above. The preferred material for forming files used to clean the operative middle portion of root canals is stainless steel. Other metals can also be used such as nickel/titanium; however, it may be necessary to design the files to have larger diameters than files formed from stainless steel when using nickel/titanium as nickel/titanium tends to be more flexible than steel. Alternatively, the files can be formed from suitable non-metal materials, such as a plastic.

When the files are formed from stainless steel or a material with comparable properties, the top end diameter of each file, where the abrading portion terminates, may range from about 0.25 mm to about 2 mm. However, the diameter will more typically range from about 0.4 mm to about 1.7 mm and most typically from about 0.5 mm to about 1.6 mm. Additionally, when the files are formed from stainless steel or a material with comparable properties, the tip diameter of each file may range from about 0.06 mm to about 0.4 mm. More typically, however, the tip diameter will range from about 0.08 mm to about 0.15 mm and most typically from about 0.10 mm to about 0.13 mm.

The length of each file in the set used to clean the operative middle portion depends on the length of the tooth being cleaned. As discussed above, after identifying the length of the root canal from an x-ray image, the length of the file to be used in the operative middle portion is determined by subtracting at least 3 mm from this identified length of the root canal. To accommodate the various root canal lengths which may be encountered, it is preferred to have files with lengths ranging from about 8 mm to about 35 mm. However, files with lengths ranging from about 10 mm to about 30 mm are most frequently utilized and files with lengths ranging from about 18 mm to about 30 mm are the most frequently utilized.

As discussed above, each file 14a–d of each file instrument 10a–d in set 10 has a length that is only sufficient to enable the file to contact the operative middle portion and the operative coronal portion of the root canal. The file length of files 14a–b enables a practitioner to aggressively clean the operative middle portion without worrying that the instrument will overly thin the root canal, perforate the apex or that cleaning will cause extrusion of material through the apex. Another benefit of cleaning the operative middle portion 262 first is that the apical portion 264 is then generally more accessible and easily cleaned. Additionally, since instruments are selected for use in cleaning the operative middle portion 262 which have files lengths that do not permit entry into the apical portion 264, the likelihood of jamming or breaking a tip of an instrument while working in the confined space of the apical portion 262 is prevented.

By instrumenting in the operative middle portion 262 and the operative coronal portion 260 before cleaning the apical portion, the practitioner can use an instrument that is relatively flexible compared to the conventional instruments. As shown in FIG. 2B, which is a cross-sectional view taken along cutting line 2B—2B of tooth 240 in FIG. 2A, file 14a of file instrument 10a is sufficiently flexible to be flexed against any surface of operative middle portion 262 or operative coronal portion 260 and yet is sufficiently rigid to remain flexed against the surface during a cleaning motion such as a longitudinal motion, a rotational motion or a reciprocating rotational motion.

File instrument 10a is shown in FIGS. 2A–2B being moved in a longitudinal movement or up and down movement as well as being rotated while file 14a is flexed or arched to urge the file against the root canal surfaces. As shown, the configuration and mechanical properties of the files used to clean the operative middle portion 262, and preferably the operative coronal portion as well 260, enable a practitioner to move the files around the perimeter or from side to side to contact the perimeter. Such movements enable the file to follow the contours of the root canal. Further, since the file is moved around the perimeter, the file has more than one center of motion during cleaning of the operative middle portion of the root canal, such as a pivot point or center of rotation, as the tip of the file or at least a part of the abrading portion does not generally remain primarily in one position.

In addition to cleaning a root canal, the instruments also simultaneously shape the root canal for subsequent filling with a filling material such as gutta percha. Cleaning and shaping a root canal generally necessitates the widening of portions of the pulp canal and smoothing some contours of the pulp canal to yield a wider and smoother canal. The amount of dentin removed during the cleaning and shaping is preferably no more than just sufficient to adequately shape the root canal for subsequent filling.

Once the cleaning and shaping of root canal 252a is completed, it appears as shown in FIG. 2C. FIG. 2C is a transverse cross-sectional view of root canal 252a taken along cutting line 2C—2C in FIG. 2A through cementum 248 and dentin 244. In addition to depicting the configuration of the cleaned and shaped root canal after file 14a has been removed, FIG. 2C also shows in phantom lines the original configuration of the perimeter of the pulp canal 252a. Note that shaped walls 268a generally have the same laminar shape as did the walls of pulp canal 252a before being cleaned and shaped.

Due mainly to the configuration and mechanical properties of the files, the contours of the operative coronal portion and the operative middle portion can be used during the cleaning by a practitioner as a guide for the movements of the files as the files are pushed against the surfaces of the root canal and simultaneously moved around the perimeter or periphery of the root canal until the practitioner has reached the beginning location of the cleaning and shaping process. By adapting to the perimetrical or perimetral anatomy of the root canal, the entire perimeter or substantially all of the perimeter is contacted and cleaned along the length of the perimeter without significantly altering the configuration of the perimetrical anatomy such that the original anatomy of the root canal or shape of the perimeter is essentially maintained. For example, in root canals that are laminar such as the cross-sectional shape of pulp canal 252a shown in phantom lines in FIG. 2C, the files can be urged along one side and then along the next side wall in a manner such that the resulting cleaned and shaped root canal is generally widened but has a perimeter that is still generally laminar such as shaped walls 268a as shown in FIG. 2C. Similarly, if the original shape of the perimeter of a root canal as seen from a transverse cross-sectional view is generally circular or tear shaped, then the cleaned and shaped walls will also be generally circular or tear shaped. In other words, the original anatomy of the root-canal controls the shape of the resulting cleaned and shaped anatomy due to the cleaning techniques enabled by the present invention.

Since a perimetrical anatomy that was primarily tubular or laminar will be enlarged but will still be primarily tubular or laminar, the tooth is less likely to be weakened as compared with prior art methodologies. As discussed above, prior art methods yield a final anatomy that is dictated by the shape of the instrument and result in the formation of a borehole in the root canal that obviously corresponds to the shape of the file. Forming a significant footprint in a root canal from the use of instruments in accordance with prior art methodologies not only weakens a tooth, it also increases the risk that the tooth can be overly thinned or that perforations may result. Additionally, such prior art methods fail to fully clean the root canal since significant portions of the perimeter are not even contacted by the instruments along the length of the root canal.

Cleaning the root canal, particularly the operative middle portion, without substantially altering the anatomy of the root canal results in a lesser likelihood of overly thinning the root canal or causing lateral perforations as compared with prior art methods. The likelihood of such complications occurring during instrumentation of the operative middle portion is further diminished since the instrument does not extend into the apical portion. This understanding enables a practitioner to more confidently urge a file such as file 14a against all surfaces of root canal 252 and aggressively clean all of the surfaces of operative middle portion of the root canal.

Another advantage of the configuration and mechanical properties of operative middle portion instruments, such as file 14a shown in FIGS. 2A–2B, is that the file can simultaneously abrade both operative coronal portion 260 and operative middle portion 262. The files can simultaneously abrade both portions as each file has an abrading portion along their entire length or along substantially all of their length. A primary benefit of simultaneously abrading both portions is the ability to farther straighten the operative coronal portion 260 while cleaning the operative middle portion 262.

Use of files in the operative middle portion which have an abrading portion along their entire length or along substantially all of their length such as abrading portions 19a–d is in contrast to files formed in accordance with ISO standardization. ISO standardized files have abrading portions of up to 16 mm and the remainder of the file is a smooth shank. Since such files are inserted down to the apex, it is generally not possible to abrade any portion beyond the anatomical root canal. Additionally, since such ISO standardized files frequently fail to remove interferences extending from the access or root chamber above the anatomical root canal, the instrument must bend around the interferences, thereby further increasing the likelihood of wall perforations, over-thinning and failing to clean significant portions of the canal. Use of such conventional instruments especially increases the likelihood of iatrogenic modifications resulting from the tip of the file.

The abrading portions 19a–d extend along most of the length of each file 14a–d. As shown in reference to FIG. 4, files 14a'–14c' may also be provided with abrading portions 19a'–19c' that extends along their entire lengths. The advantage of files having a shank portion such as shank portions 16a–d include the ability to easily utilize stops or to include incremental markings on the shank portion. In an embodiment that utilizes no stops such as the files shown in FIG. 4, the length of the file and the abrading portion are the same.

Figure 4:
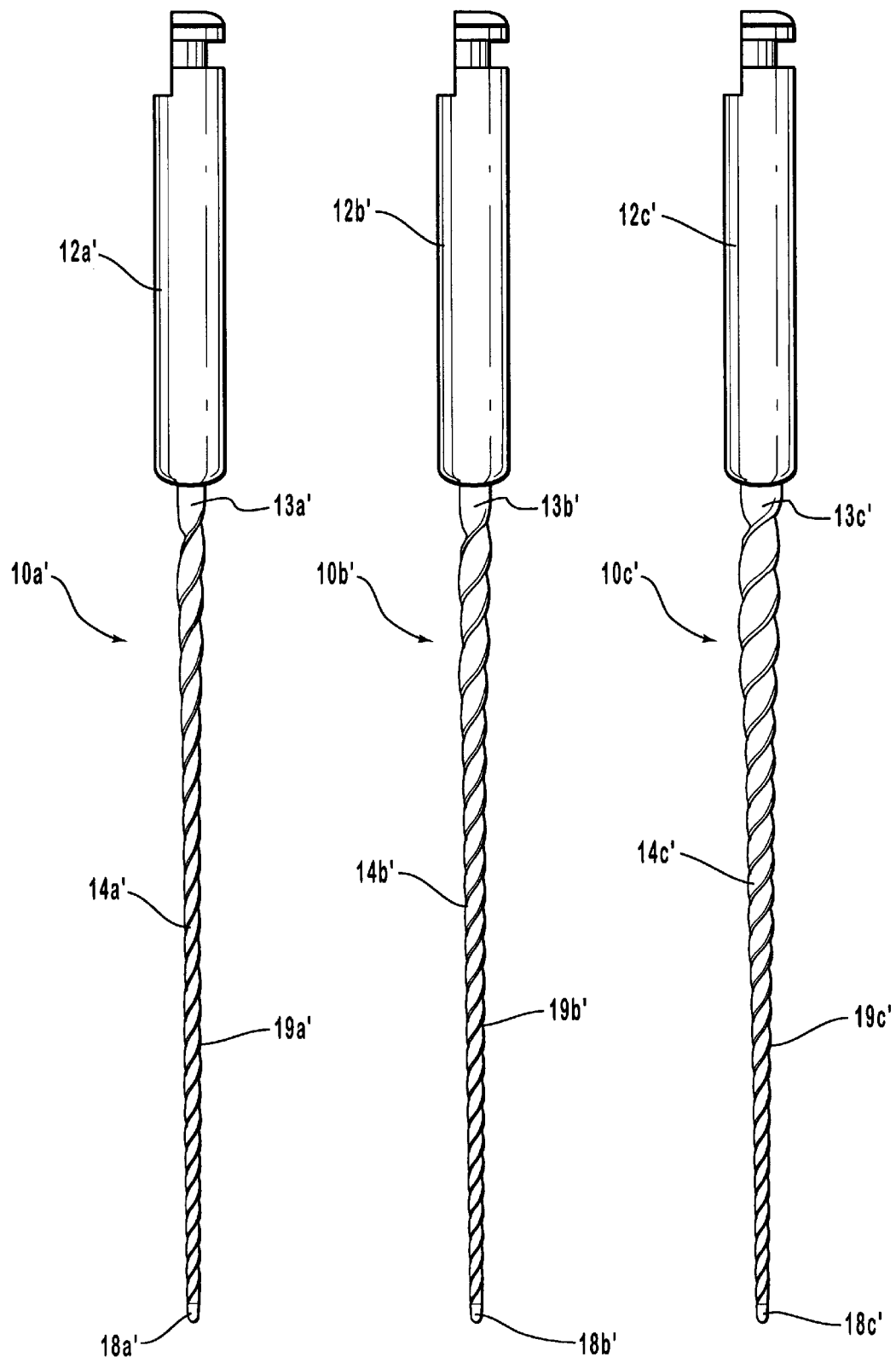
FIG. 4 is a perspective view of another embodiment of a set of endodontic instruments for cleaning of the coronal portion and operative middle portion of a root canal.

The abrading portion is at least the outer edge of the file. The abrading portion of the files in FIGS. 1 and 4 are formed by twisting a blank such as a rectangular blank. Conventional techniques such as twisting, cutting and appropriately machining a precursor blank to form abrading portions such as cutting surfaces or helical features with the appropriate screw periodicity can be utilized alone or in combination. The abrading portion can also be formed by cutting lands in a precursor blank having three or four sides or a cylindrical rod. A precursor blank or rod may also be abraded to impart a roughened surface. Additionally, the file may have an abrading portion that is a knurled surface. Any conventional methodology may be used to form the abrading portion and the file may have an abrading portion that appears like conventional K-files or Hedstrom-type files.

While the files may have any suitable transverse cross-sectional shape, they are preferably configured in a manner such that the potential for breakage is minimized. For example, a file with a square cross-section may be preferred over a triangular cross-section as the file with a square cross-section has a greater mass and is accordingly less likely to break. Additionally, a file configured with tines or extensions having wide angles are generally preferred over those with narrow angles. However, the preferred tine configuration depends primarily on the particular use as in some instances it is desirable to aggressively cut while in others the root can be more passively cut. When it is more desirable to aggressively cut, it may be preferred for example to utilize a file with relatively narrow tines. As indicated above, the abrading portion may also include abrasive particles positioned on the file. One or more instruments in a set may have a file with abrasive particles while the others may have abrading portions formed by other techniques. Additionally, only a part of the file may have abrasive particles such as the upper section for more aggressive shaping or rectification of the root canal. The abrasive particles are preferably diamonds. The application, impregnating, coating or attachment of the abrasive coating may be achieved by any conventional method. All of the files in combination with their respective abrading portions disclosed herein are examples of means for removing and cleaning of pulp material as the file instrument is operatively moved. Additionally, each abrading portion disclosed herein is an example of a means for abrading a root canal.

File instrument 10a is preferably used in conjunction with an endodontic handpiece designed for movement of endodontic file instruments as shown in FIGS. 2A–2B at 100. The endodontic handpiece 100 and file 10a are drawn in phantom lines to represent the ability of the file to be moved and flexed as root canal 252a is cleaned. File instrument 10a can be continuously rotated in one direction only or file instrument 10a can be rotated in a reciprocating motion such that file instrument 10a rotates for example, clockwise for half of a revolution and then counterclockwise for half a revolution. A reciprocating motion is preferred as such motion enables the file to alternately engage material 250 and the walls of the operative middle portion of the root canal in a manner that removes material 250 and to then rotate in the opposite direction such that the file less aggressively engages material 250 and the operative middle portion walls, depending on the file design. Accordingly, rotating file instrument 10a in a reciprocating motion minimizes breakage of file 14a when file 14a encounters a surface that prevents rotation of file instrument 10a in a direction that enables cleaning and removal of material 250. File instrument 10a can also be vibrated or manipulated by hand. Hand milling is, however, more difficult and time consuming.

The optional stop 140 shown being utilized is generally not necessary since the file length can be selected to correspond closely with the combined length of the operative coronal portion and the operative middle portion. Stops such as stop 140 may be used to ensure that the length of the portion of the file inserted into the tooth is such that the file does not extend significantly into the apical root portion. The advantage of using such a stop is that less sets of instruments are needed in order to have a set that can be utilized in teeth of varying lengths. Accordingly, files 10a–d have shank portions 16a–d that are preferably in a range from about 2 to about 4 mm in length and that are more preferably about 3 mm long to enable stops to be positioned as needed. Note that while a stop is shown with a thickness of about 1 mm, stops may have varying thickness. Also, the stops may also be positioned such that one or more stops are positioned adjacent to the handle such that movement is not possible since the stops already abut the handle. All of the stops disclosed herein are examples of stop means for limiting the operative middle portion instrument means to insertion into the operative coronal portion and the operative middle portion.

When a stop is used, the length of the root canal from an x-ray image is first identified and then the length of the root canal above the apical root portion is determined by subtracting 3 mm from this identified length of the root canal. An instrument is then selected that has a length that is slightly longer than the determined length of the root canal down to the apical portion. Note that this determined length is the combined length of the coronal portion and the operative middle portion.

It may also be advantageous to use a stop such as stop 140 to more easily flex the file against the root canal surfaces. More particularly, using an instrument with a stop alters the curvature of the file since the portion above the stop is also flexed. This results in a different flexed configuration or pivot point so that greatest pressure is applied at a higher part of the root canal than when an instrument is used without stops. The desirability of applying pressure in such a manner depends on the particular tooth. Note however that if an instrument is used without a stop then the portion of the file that is flexed against the root canal can also be used to abrade sections thereabove by merely moving the file upward as it is flexed. Whether a stop is used or not, the file can always be moved further above the apical portion so that it is easier to arch the file. For example, FIG. 2B shows tip 18a of file 14a nearly reaching the apical portion 264 and also shows file 14a in phantom after being moved higher in root canal 252a and being more significantly arched.

It is also possible to utilize the file instruments with a unique handpiece such as is disclosed in U.S. patent application Ser. No. 09/639,699 entitled Endodontic Instruments Adapted to Provide Variable Working Lengths and Related Methods for Using the Instruments which was filed on Aug. 16, 2000 by Francesco Riitano and Dan E. Fischer and is owned by Ultradent Products, Inc. Ser. No. 09/639,699 was filed as a continuation-in-part application of U.S. patent application Ser. No. 09/425,849 entitled Incrementally Adjustable Endodontic Instruments which was filed on Oct. 22, 1999 by Dan E. Fischer and is owned by Ultradent Products, Inc. Ser. No. 09/639,699 and Ser. No. 09/425,849 are hereby incorporated by reference. The handpiece 100 shown in FIGS. 2A–2B corresponds with the handpieces disclosed in Ser. No. 09/639,699 and Ser. No. 09/425,849. One of the advantages of handpiece 100 is that all of its bottom surfaces are essentially coplanar so that its rim may be used as a stop as it is rested on the coronal surface of tooth 240. The ability to use the rim as a stop eliminates the need for rubber stoppers. Although, it is not necessary to use a stop when using instruments adapted for use with handpieces as disclosed in the above-identified applications, a stop is shown being used in FIGS. 2A–2B in order to illustrate the use of stops with handpieces in general. Another advantage of handpiece 100 is that the position of handle 12a may be adjusted relative to the chuck as the chuck applies mechanical pressure against handle 12a to hold handle 12a within the chuck. Chuck 100 enables handles to be held whether they have a latch such as the latch-type handles 12a'–c' designed for coupling with a conventional handpiece or do not such as those shown in FIG. 1 at 12a–d.

Set 10 is shown with four instruments, however, more instruments may be included so that there is a more gradual increase in rigidity and ability to aggressively abrade the root canal as the instruments are sequentially utilized. Also, as shown by set 10' it is also possible to utilize less instruments. Advantages of using a set with less instruments is that the set is less expensive and is simpler to use than sets with more instruments. The set may even include only two instruments or only a single instrument may be utilized to clean the operative middle portion. Accordingly, instruments such as instruments 10a–d or 10a'–c' may be used alone or as part of a set to remove and clean essentially all pulp material from the operative coronal portion and the operative middle portion. Such instruments as well as sets that includes such instruments are additional examples of first endodontic instrument means for anatomically removing and anatomically cleaning essentially all pulp material from the operative middle portion without significantly extending into the apical root portion.

The apical portion, as discussed above, is the location in the root canal of most complications that occur during a root canal cleaning procedure. The greatest likelihood for the occurrence of complications such as over thinning of root canal walls, perforation or extrusion of material from the canal is in the apical portion. The apical portion is the most likely site for such complications as apical portions are more complex and delicate compared to the operative middle portions of teeth. Since such complications are most likely to occur in the apical portion, it is advantageous to simplify and ease the cleaning of the apical portion by first cleaning the operative middle portion.

It is also highly beneficial to have the material removed from the operative middle portion in order to minimize the amount of material that can come out of the root canal to cause problems. Since the majority of bacteria in an infected root canal is typically located in the operative middle portion, removal of pulp material 250 from operative middle portion 262 removes the majority of bacteria in the pulp canal. Not only is the greatest volume of bacteria in the operative middle portion but it is also believed that the concentration is greater in the operative middle portion. Since a certain minimum threshold must generally be reached for complications to arise due to microbial presence in a root canal, removal of the pulp material in the operative middle portion before cleaning the apical portion significantly reduces the likelihood of complications such as exposing the surrounding tissue to bacteria due to overly thinning the root canal, perforation or extrusion of material from the canal. For example, in the event of an apical extrusion far less septic material may be expressed during instrumentation in accordance with present methodology than if the apical extrusion occurred as a result of cleaning in accordance with conventional methods wherein files are inserted to the apical portion before cleaning the operative middle portion. As a result, removal of the majority of bacteria before cleaning the apical portion increases the likelihood of successful root canal therapy in several ways compared with conventional methods. More particularly, since the aggressive cleaning motions do not occur in the apical portion, the likelihood of complications is decreased and if a complication does occur in the apical portion it is less likely to result in failure of the procedure.

Since the majority of bacteria in an infected root canal is typically located in the operative middle portion, it has been found that after the operative middle portion has been cleaned in an abrasive manner effective root canal procedures can be completed by cleaning the apical portion without abrading the apical portion. More particularly, after removing and cleaning essentially all pulp material from the operative middle portion of an operative root canal in conformance with the anatomical shape of the operative middle portion by flexibly moving an instrument within the operative middle portion, the root canal procedure can be effectively completed by merely irrigating the apical portion of the root canal and then removing the irrigant and debris. This eliminates the possibility of exposing the surrounding tissue to bacteria due to overly thinning or perforating the apical portion of the root canal and minimizes the possibility of extrusion of material from the canal. Since such complications typically occur during abrasive instrumentation within the apical portion due to the delicate and complex structure of the apical portion, the elimination of the need for abrasive instrumentation in the apical portion is highly advantageous. Further, this methodology is particularly advantageous in light of the prior cleaning of the root canal above the apical portion.

Another benefit of cleaning the apical portion by irrigating the apical portion with an irrigant and then removing the irrigant and debris from the apical portion, is the reduction in the number of instruments needed to complete the procedure. More particularly, since instruments adapted for abrading the apical portion are not necessary but are optionally used, the total instruments used in performing root canal procedures is reduced.

In addition to cleaning the apical portion, irrigation is used to maintain the smear layer in solution within the apical portion, thereby avoiding smear layer accumulation. Additionally, it is useful to maintain the debris derived from cleaning the root canal in suspension to avoid filling the apical portion of the root canal with a plug. If the apical portion becomes filled, there is an increased likelihood that the progression may be prevented or that debris may be pushed out of the tooth.

Figure 5A:
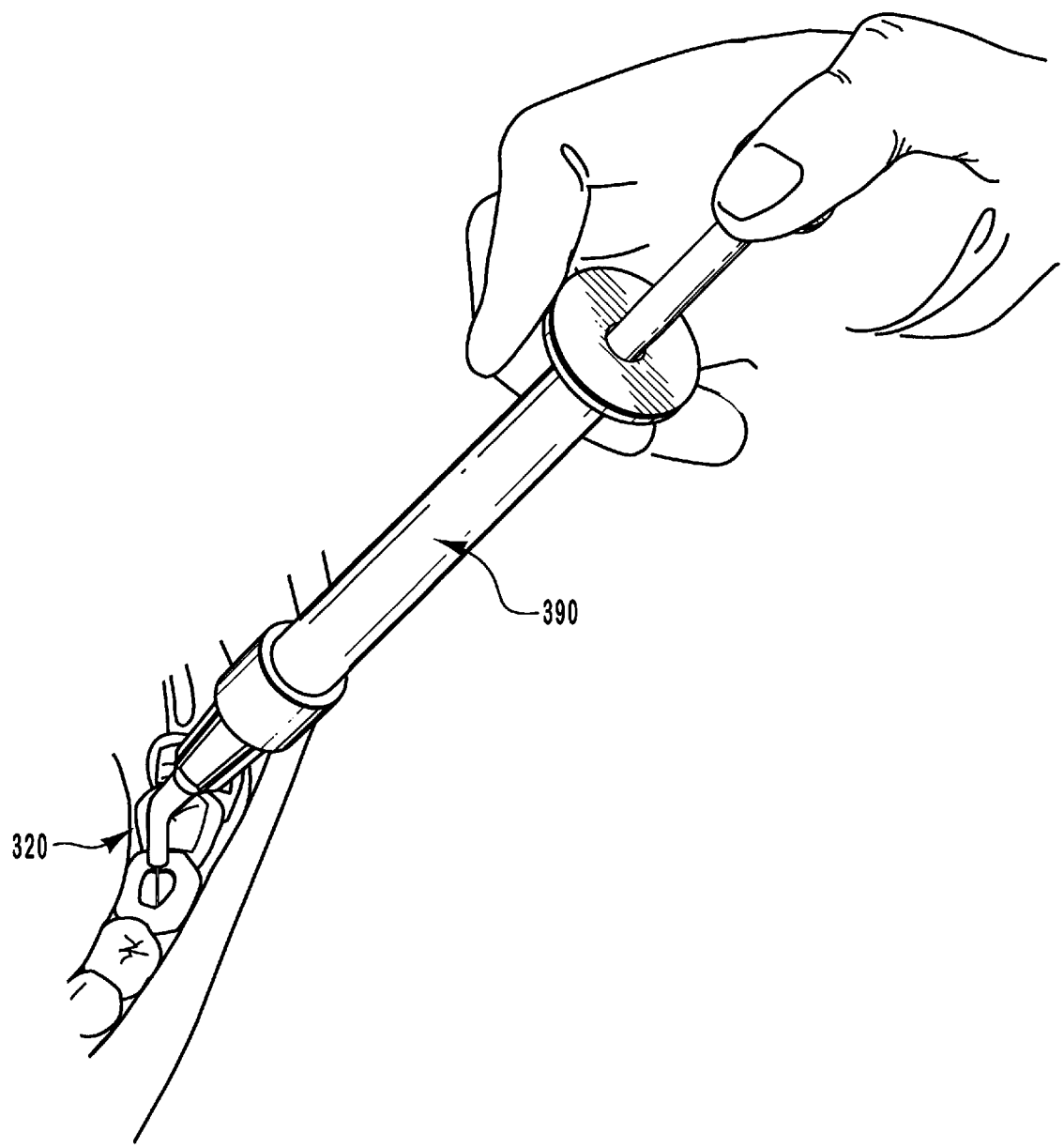
FIG. 5A is a depiction of a practitioner employing an endodontic irrigation tip to demonstrate the convenience of employing the angled tip.
Figure 5B:
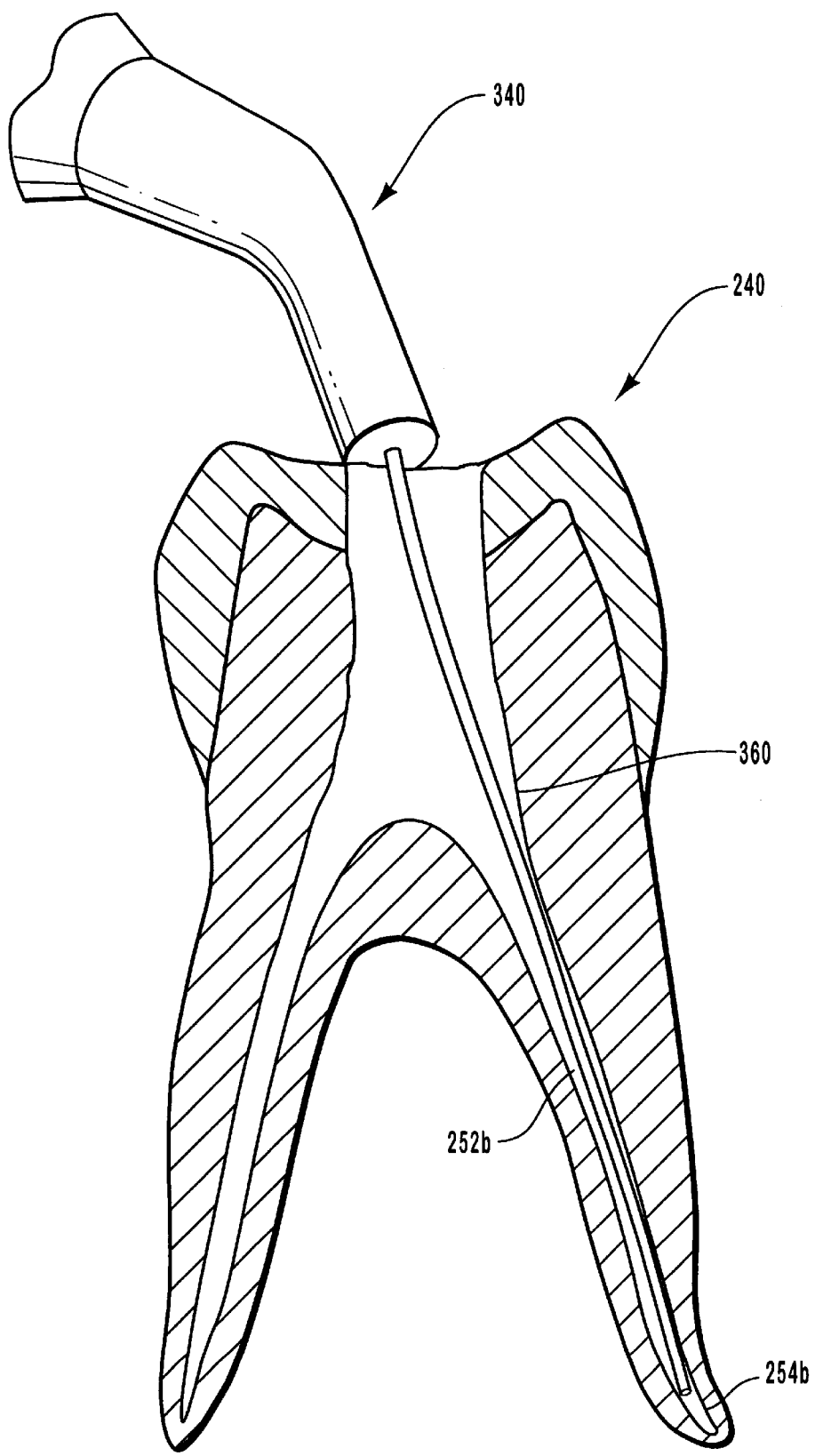
FIG. 5B is a view of a cross section of a tooth with the apical root portion being irrigated by the endodontic irrigation tip shown in FIG. 5A.

The irrigant may be delivered from an irrigation tip such as angled irrigation tip 320 as shown in FIG. 5A which is attached to a syringe 390. FIG. 5B shows cannula 360 of irrigation tip 320 extending down into apical portion 264 in close proximity to apex 254b of root canal 252b. Such angled irrigation tips are disclosed in greater detail in U.S. Pat. No. 6,079,979 entitled Endodontic Irrigator Tips and Kits which issued to Francesco Riitano and is owned by Ultradent Products Inc.; the disclosure of which is hereby incorporated by reference. Another preferred irrigation tip is the Endo-Eze(®) irrigator tip sold by Ultradent Products, Inc which has a straight cannula or needle. Examples of suitable Endo-Eze® irrigator tips include those which have a 27 gauge cannula (0.40 mm out diameter), 30 gauge cannula (0.30 mm outer diameter) and a 31 gauge (0.25 mm outer diameter). In some circumstances, larger needles may be used. In any event, the needle or cannula is preferably sufficiently small to avoid binding within the cannula and also to enable backflow for flushing the apex. While such particular irrigation devices are preferred, any conventional irrigation tip and associated delivery device such as a syringe may be utilized. Other apical portion cleaning instruments can also be utilized such as pipettes. The irrigator tips disclosed herein and other suitably shaped narrow tubular devices, are examples of means for cleaning the apical root portion, after the pulp material has been essentially removed from the operative middle portion. More specifically, the irrigator tips are examples of means for cleaning the apical root portion by delivering an irrigant into the apical root portion.

In addition to syringes, such irrigator tips may be coupled to a Stropko device such as the delivery device disclosed in U.S. Pat. No. 5,378,149 issued to John J. Stropko which is hereby incorporated by reference. Syringes and the Stropko device are examples of delivery devices. These same devices are examples of irrigant delivery devices when coupled with an irrigator tip that enables the delivery devices to easily access the root canal. While these irrigant delivery devices are particularly useful when cleaning the apical portion, all of these irrigant delivery devices may also be used in irrigating the canal at any appropriate time during the root canal procedure. Note that syringes and other delivery devices such as a Stropko delivery device are examples of means for delivering irrigants and/or removing irrigants and any remaining debris via the irrigator tip or means for cleaning the apical root portion.

Pipettes are a less preferred alternative to the use of irrigation tips as apical portion cleaning instruments to deliver irrigants into the root canal. Such conventional pipettes are well known in endodontistry and are used to deliver irrigants by squeezing part of the pipette. The pipettes may be prefilled or used with a separate reservoir or container of lubricant. A pipette is an example of an integral irrigant delivery device while an irrigator tip coupled to a syringe or a Stropko device is an example of a separable irrigant delivery device. Such integral irrigant delivery devices are additional examples of means for cleaning the apical root portion or more specifically, means for cleaning the apical root portion by deliverying an irrigant into the apical root portion.

These same irrigant delivery devices are typically used to remove the irrigant and any remaining debris. For example, the syringe may be used to aspirate the irrigant and any remaining debris out of the apical portion. Similarly, a pipette may apply appropriate suction to remove the irrigant and any remaining debris. The endodontic irrigator tip may also be coupled to other conventional aspiration devices. Other irrigant removal devices include conventional paper points.

Although, the irrigant preferably is capable of dissolving or disrupting soft tissue remnants to permit their removal, the irrigant may be any suitable liquid such as water or various alcohols. More particularly, although some degree of debridement is preferred, any fluid may be used to flush debris from the root canal. General examples of appropriate irrigants include hydrogen peroxide, primarily for use in the canals of living teeth, or sodium hypochlorite, primarily for the canals in necrotic teeth. The preferred irrigant is the aqueous sodium hypochlorite solution sold as ChlorCid® by Ultradent Products, Inc which contains about 2.5–3% NaOCL. The irrigant may also be a chelator or calcium remover such as EDTA solutions or citric acid solutions. A preferred chelator is sold as File-Ezet by Ultradent Products Inc. which is a 19% EDTA water soluble viscous solution. File-Eze® is a preferred chelator as it is also a lubricant.

As indicated above, it may be necessary in some circumstances to improve the access into the apical root portion before cleaning the apical root portion of the root canal. More particularly, it may be beneficial or necessary to widen the tract of the root canal to provide access for thin irrigation needles. This may be achieved by widening the transition between the operative middle portion 262 and the apical portion 264 or by widening the entire apical portion such that a thin irrigation needle can access the apical portion as needed. Thin irrigation needles typically have a diameter no smaller than about 0.30 mm so it may be necessary to increase the diameter of portions of the root canal up to about 0.35 mm or even up to about 0.40 mm, particularly within the region of the boundary between the operative middle portion and the apical root portion. Note that the diameter need only be slightly larger than a thin irrigation needle in order to provide adequate access. Improving access into the apical portion not only enables such irrigation needles to move as needed, it also reduces the likelihood that the thin irrigation needles will be blocked. Although FIG. 3 depicts file 74d inserted into apical portion 264 of root canal 252a and cleaning the apical portion, use of instruments 40a or 40b of optional set 40 is achieved in essentially the same fashion. When utilized to widen the access into the apical root portion of a root canal, file 40a is first introduced followed sequentially by file 40b.

Instrument 40a has a file 44a with smooth shank portion 46a, a square portion 47a, an abrading portion 49a and a file tip 48a. As shown, the smooth shank portion 46a is the top section of file 44a and a handle 42 is positioned on shank portion 46a. Smooth shank portion 46a tapers to square portion 47a which is between shank portion 46a and abrading portion 49a. A file instrument such as file instrument 40a or a set of file instruments such as 40a and 40b comprises a second endodontic instrument means for improving access into the apical root portion after the pulp material has been essentially removed from the operative middle portion by the first endodontic instrument means.

It is not necessary for the entire apical portion to be widened up to about 0.35 mm or about 0.40 mm; just enough of the apical portion should be widened so that the irrigants can be delivered as needed. However, the length of files used to widen the apical portion is preferably sufficient to at least approximately reach the apex. Accordingly, the top of the abrading portion may be flared to enable the upper area of the apical portion to be widened up to about 0.40 mm while the tip diameter which is at or near the apex is preferably significantly smaller. Note that in addition to abrading at least the top of the apical portion, it may also be necessary to widen the diameter in the region of the base of the operative middle portion. Before widening the apical portion of the root canal, it is preferable to make a predetermination of the desired diameter. This predetermination is preferably made in light of morphometric data such as average diameters, wall thicknesses, etc. for the particular root canal being cleaned.

As indicated above, the length of a file such as files 44a and 44b is preferably sufficient such that when the file is inserted into the root canal the tip can at least approximately reach the apex and the abrading portion of the file can improve the access into the apical portion of the root canal. Although files used to improve the access into the apical root portion may be long enough to approximately reach the apex, the files can be used to improve the access as long as the files can reach the bottom of the operative middle portion and the top of the apical root portion. Such file lengths are typically within a range from about 8 mm to about 35 mm, more typically in a range from about 14 mm to about 35 mm and most typically in a range from about 12 mm to about 33 mm.

Each file of the file instruments designed for improving access to the apical root portion of a root canal is configured to have an abrading portion such as abrading portions 49a–b along at least a portion of the length of the file. The entire length of each file can be configured with an abrading portion, however, the abrading portion preferably extends from the tip part way upward towards the top end such that the remainder of the file is relatively smooth. More particularly, each file is preferably configured with an abrading portion along less than about half of the length of the file and more preferably about one-third of the length between the tip and the top end. The abrading portion is preferably long enough so that the entire apical portion can be abraded as well as at least the bottom of the operative middle portion. The length of the abrading portion is generally within a range from about 1 mm to about 35 mm, preferably in a range from about 2 mm to about 16 mm, more preferably in a range from about 3 mm to about 10 mm, and most preferably in a range from about 5 mm or about 6 mm Note that stops such as stop 140 may alternatively be utilized with instruments used to improve the access into the apical root portion. The abrading portions may have a similar or identical configuration to the abrading portions disclosed herein for cleaning either the operative middle portion of the root canal or the apical root portion.

In an optional set of instruments used to improve the access into an apical root portion, the file tips of the instruments preferably all have about the same diameter. The diameter of the tips, such as the diameter of tips 48*a–b*, is generally within a range from about 0.06 mm to about 1 mm, however, the tips preferably have a diameter of about 0.08 mm. In a less preferred embodiment, the tip diameter of each file may also increase sequentially. The tips can have a similar or identical configuration to the tips of the files disclosed herein for cleaning either the operative middle portion of the root canal or the apical root portion. However, the tips are preferably rounded.

The diameter of the abrading portions preferably increases from the tips towards the top of the abrading portions. The diameter of the abrading portion at the top is preferably within a range from about 0.1 mm to about 0.4 mm and is more preferably in a range from about 0.25 mm to about 0.4 mm Each successive file preferably has an abrading portion which is successively larger in diameter at the top of the abrading portion than the abrading portion of the preceding file. Accordingly, a set may have files with abrading portions having the following respective top diameters: about 0.2 mm, about 0.25 mm, about 0.3 mm and about 0.35 mm. Each abrading portion in such a set has a different taper. The abrading portion may also have essentially the same taper so that the taper of the shank portions remains essentially constant as the different files in the set are sequentially inserted. However, the abrading portions and the shank portions of the files may have any suitable configuration.

As mentioned above, the apical portion may be alternatively cleaned by abrading the apical portion. Typically, the instruments used to optionally improve the access into the apical portion, the apical portion access instruments, have the same lengths as the instruments optionally used thereafter to abrade the apical portion so that the entire apical portion is first widened and then cleaned in an abrasive manner. The instruments, however, have different tip diameters and tapers along their respective abrading portions. The apical portion access instruments generally have much smaller tip diameters and much greater tapers than the instruments used to abrasively clean the apical portion. Refer to Example 1 for a discussion of specific instruments utilized and to observe the alteration of the apical portion after the apical portion widening phase and the apical portion cleaning phase.

The apical portion cleaning instruments are preferably more flexible than the instruments used to clean the operative coronal portion and the operative middle portion since the apical portions tend to be more curved. While stainless steel may be utilized, the files are preferably formed from nickel/titanium or a stainless steel alloy such as a precipitation hardenable stainless steel, particularly 17–4PH stainless steel that has not been aged or subjected to heat treatment. While files can be formed from these same metals that are utilized in the operative coronal portion and the operative middle portion, such metals are particularly suited for use in the apical portion as such metals provide optimal flexibility. Note also that the apical portion cleaning instruments are typically manually moved so that these flexible files can be carefully maneuvered. The instruments used to optionally improve the access into the apical portion may also be formed from any of these metals.

Before the apical root portion is abrasively cleaned, it is preferable to obtain further x-ray images while an instrument is inserted into a root canal to determine the desired working length of the instrument. In establishing the working length, the state of the apex and the periapical tissues should also be evaluated, in accordance with the following guidelines. For living or necrotic teeth "without rearrangement of the apex" or apical rarefaction, the instrument(s) should be kept no closer than 2 mm from the apex as shown on the x-ray image. Conversely, for necrotic teeth with apical autolysis, the preparation work may be performed up to a distance of 1 mm from the apex as shown on the x-ray image. The predetermination of the widening of the canal leading to the apex, and the widening of each root canal for polyradiculated teeth, should be made bearing in mind typical morphometric configurations.

In most cases, the radicular apex contains the final segment of the main canal, which divides into a delta configuration. This structure is hard to detect with x-rays. Therefore, the morphology of the dental apex is unpredictable, and the location of the junction between the cementum and dentin in any endodontic apex is random Likewise random is the hypothetical apical constriction that can be detected by the most expert professionals. A degree of confidence can be obtained through the use of electronic measurement devices in living canals that have not been treated with liquid medications, but only when the foramen has been passed, in order to be subsequently withdrawn into the canal with a probe instrument. This maneuver should be avoided in necrotic canals, because of the risk of carrying germs beyond the apex.

The guidelines discussed above should be kept in mind when redetermining the approximate working length to the apex after the operative middle portion has been prepared. It is necessary to redetermine the working length as the working length has likely changed due to the instrumentation of the operative middle portion.

Set 70 is shown with twelve instruments. However, in use only 1–3 instruments are typically utilized. If a file is inserted and it is apparent to the practitioner that the file is not engaging the walls of the root canal in the apical portion, then a larger file is inserted. While instrumenting the root canal with only this instrument may be sufficient, it is often necessary to utilize one or two additional instruments with successively larger files. So for example, if file 70*b* or 70*c* is first introduced into the apical root portion then it is followed by then next larger file such as 70*c* or 70*d*.

Each file instrument 70*a–l* comprises a handle 72*a–l* connected to a file 74*a–l*. Each file 74 has a top end where the file joins handle 72. Each file terminates at a tip 78*a–l* located opposite the top end of the file. Each file 74 has a smooth shank portion 76, a square portion 77 and an abrading portion 79. A file instrument such as file instrument 70*a* or a set of file instruments such as 70*a–l* comprises a third endodontic instrument means for optionally, abrasively cleaning and removing essentially all remaining pulp material from the apical root portion after the pulp material has been essentially removed from the operative middle portion. Note that the endodontic instrument means for abrasively cleaning and removing essentially all remaining pulp material from the apical root portion after the pulp material has been essentially removed from the operative middle portion and the means for cleaning the apical root portion by delivering an irrigant into the apical portion after the pulp material has been essentially removed from the operative middle portion are both examples of means for cleaning the apical root portion after the pulp material has been essentially removed from the operative middle portion.

Exemplary dimensions of files 70*a–l* are provided below in detail in Example 1 of the Examples of the Preferred Embodiment. The file of each apical portion file instrument is an example of operative apical portion instrument means for movement within the apical root portion so as to effect removal and cleaning of pulp material as the file instrument means is operatively moved.

Each file 74 of the file instruments designed for abrasively cleaning the apical root portion of a root canal is configured to have an abrading portion 79 along at least a portion of the length of file 74. Like files 44, the entire length of each file 74 can be configured with an abrading portion 79, however, abrading portion 79 preferably extends from tip 78 part way upward towards top end 73 such that the remainder of file 74 is relatively smooth. More particularly, each file is preferably configured with an abrading portion along less than about half of the length of the file and more preferably about one-third of the length between tip 78 and top end 73. The abrading portion 79 can have a similar or identical configuration to the abrading portions of the file used to clean the operative middle portion of the root canal or to improve the access into the apical root portion.

The length of an optional apical portion abrading file such as files 74a, 74b and 74c is sufficient such that when the files are inserted into the root canal the tips can at least approximately reach the apex and the abrading portion 79 of the files can substantially contact and abrasively clean the pulp material in the apical portion of the root canal. Such file lengths are generally within a range from about 8 mm to about 35 mm, more typically in a range from about 14 mm to about 35 mm and most typically in a range from about 12 mm to about 33 mm. The length of the abrading portion is generally within a range from about 1 mm to about 35 mm, more preferably in a range from about 2 mm to about 16 mm and most preferably in a range from about 3 mm to about 6 mm. Note that stops such as stop 140 may alternatively be utilized with instruments used to abrasively clean the apical root portion.

The diameter of the abrading portion is generally within a range from about 0.06 mm to about 1.4 mm. As shown in FIG. 1, each successive file has an abrading portion, identified as 79a–l, which is successively larger in diameter at the top of the abrading portion than the abrading portion of the preceding file.

The diameter of the tips 78a–c of each optional apical portion abrading file may be increased incrementally such that each sequentially utilized abrasive cleaning instrument has a slightly larger tip diameter than the preceding instrument as shown in FIG. 1 or the tips diameters may be about equal in diameter. Tips 78a–l can have any configuration, however, tips 78a–l are preferably rounded with minimal cutting capability to decrease the likelihood of ledging.

The diameter at the top end of the file is shown being greater than the diameter of the abrading portion. However, the diameter at the top end of the file can also be equal to or less than the diameter of abrading portion 79 or tip 78.

Note that all of the abrading portions 79a–l of files 74a–l may have the same taper or a set may include files with abrading portions having more than one taper. The taper may also increase from file to file. In a preferred embodiment, however, the last file used to instrument in the apical portion preferably has a taper that is greater than the conventional ISO taper of 0.2 to enable the gutta percha points having a taper of 0.2 to be easily inserted.

The abrading portions of files used to clean the apical portion or to improve the access into apical portion may be formed in any manner such as those described above in reference to the abrading portions of files used to clean the operative middle portion. The abrading portion 79 preferably has few spirals such that the action of abrading portion 79 against the walls or surfaces of the apical portion of the root canal is relatively gentle. Such an abrading portion is less aggressive as fewer spirals results in tines that have a wider angle.

When cleaning the apical portion 264 as shown in FIG. 3, the apical root portion file instruments are generally moved in a different pattern compared to the operative middle portion file instruments due primarily to the different perimeter anatomies of the two portions. A root canal generally becomes more cylindrical towards the apical portion such that a root canal with a perimeter anatomy that is essentially elliptical in shape within the operative middle portion tapers to an essentially cylindrically shaped perimeter anatomy within the apical portion.

Due to the more cylindrical anatomy of an apical root portion, it becomes much less necessary, and virtually impossible to flex a rotating file in a milling motion. It is generally adequate to merely rotate the file within the apical root portion and/or move the file in a longitudinal motion. More specifically, after the file reaches the apex or approximately reaches the apex, the file is preferably moved upward while simultaneously being rotated, and it is withdrawn in order to be cleaned before being reintroduced.

Since the instruments used to clean the apical portion and to improve the access into the apical portion are typically moved by hand, they have a handle adapted for such use as shown at 42a–b and 72a–72l while the instruments used to clean the operative middle portion have handles 12a–d adapted for use with an endodontic handpiece. The file instruments of the present invention can, however, be utilized with any suitable handle configuration. All of the handles disclosed herein are examples of end means for grasping and operatively moving a file in an abrasive action.

Since an apical portion file is generally not moved around the perimeter as in cleaning the operative middle portion, the center of motion, such as the center of rotation, of the file generally corresponds with the center of the root canal. In contrast, the center of motion during cleaning of the operative middle portion is at various locations as the file is moved around the root canal.

The files used to optionally clean the apical root portion in an abrasive manner can be designed for primarily longitudinal movement, rotational movement or combinations thereof Since it is generally not necessary to flex a file when cleaning the apical root portion as the apical root portion is typically more round than other sections of a root canal, apical root portion files need not necessarily have the same properties as the operative middle portion files in terms of flexibility, rigidity and resilience. The files used to clean the apical portion are, however, preferably sufficiently flexible to adjust to the anatomy or structure of a root canal in a manner that enables the tip of the file to reach the apex. The files also preferably have sufficient rigidity to apply pressure against the walls or surfaces of the root canal as the abrading portion of the file is urged against the walls of the root canal and simultaneously moved in a cleaning motion even after the file has moved throughout the length of the root canal. Additionally, a file configured for use in an apical root portion preferably has adequate resilience to avoid being substantially deformed as the file passes through a root canal and also as the abrading portion is applied against the walls of the root canal.

EXAMPLES OF THE PREFERRED EMBODIMENTS

Examples 1–2 are hypothetical examples presented solely to illustrate some embodiments of the present invention.

Note that reference is made in Example 1 to FIG. 1 and FIGS. 6A–D. Example 1 provides a discussion of the use of the three sets of instruments identified at 10, 40 and 70 in FIG. 1 to prepare a root canal. Example 2 provides a discussion of the use of set 10 to clean the operative middle portion followed by cleaning of the apical root portion through delivery of an irrigant. The shapes and dimensions of the embodiments of endodontic file instruments provided herein are merely illustrative, but not limiting, of the variety of endodontic file instruments that are manufactured according to the present invention. The hypothetical examples are not to be construed as limiting the spirit and scope of the invention as these hypothetical examples were produced in furtherance of reducing the present invention to practice.

Example 1

This example describes, in relation to FIG. 1 and FIGS. 6A–6D, an exemplary system and method for cleaning a root canal after the root canal has been properly accessed. After a tooth has been identified as requiring root canal therapy, an x-ray image is obtained in order to determine the state of health of a tooth as well as the structure and anatomical characteristics of the tooth. After all carious tissue and any old fillings have been removed, a dam is installed. The pulp chamber is then opened so that adequate access can be gained to the anatomical root canal. Access is gained by removing the top of the pulp chamber, preferably with an appropriate diamond bur instrument. The contents in the pulp chamber are then removed with the aid of appropriate irrigants. Examples of appropriate irrigants include hydrogen peroxide, primarily for use in the canals of living teeth, or sodium hypochlorite, primarily for the canals in necrotic teeth. If desired a cuspidectomy may be performed.

Figure 6A:
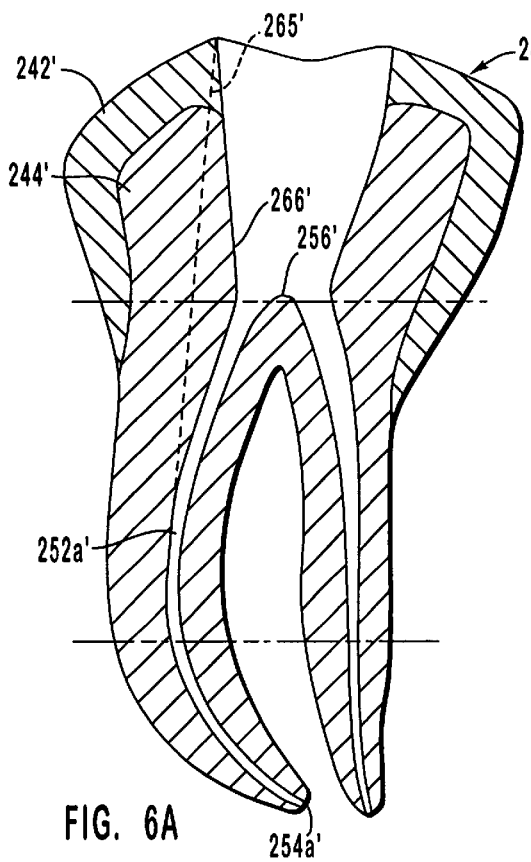
FIG. 6A is a cross-sectional view of a tooth after the pulp chamber has been accessed and before rectification.

It is then preferable to remove or reduce dentinal or enamel protrusions or irregularities such as dentinal shelves, that may obscure or hinder access of instruments into the operative root canal by rectification of such protrusions with an appropriate instrument which preferably utilizes diamonds for abrasion. FIG. 6A depicts a tooth 240' before the removal of dentinal shelf 266' above root canal 252a'. Dotted line 265' in FIG. 6A depicts the desired realignment through rectification in order to provide greater access for instrumentation during the subsequent phases. Rectified root canal 252a' depicted in FIGS. 6B–D after subsequent phases shows that rectification would enable an instrument to be inserted in a relatively straight manner though the operative coronal portion 260 and the operative middle portion 262. Although, an instrument would need to flex within the apical portion 264 of root canal 252a' due to its curvature, the required flexing is minimized as a result of the removal of dentinal shelf 266' above root canal 252a'. Since the apical portion of root canal 252b' is essentially straight, rectification of dentinal shelf 266' above root canal 252b' would also enable an instrument to be inserted down to apex 254b' through the apical portion 264' in an essentially straight configuration.

Note that pulp material is not shown in FIGS. 6A–D so that the changes to pulp canal 252a' are clearly visible after each phase. As discussed hereinbelow, FIGS. 6B–D respectively depict root canal 252a' of tooth 240' after cleaning operative coronal portion 262, after widening apical portion 264 and after cleaning apical portion 264.

After any necessary rectification, the working length is determined for the files used to clean the operative middle portion. The appropriate working length is determined by radiographically identifying the length of the operative root canal and then subtracting 3 mm from the length identified from the x-ray image. It is necessary to subtract 3 mm from the overall x-ray length in order to compensate for any distortions in the x-ray image and to avoid interfering with the apical portion while the operative middle portion is being prepared. After identifying the length of the root canal of a tooth and determining the working length of the files to be used, instruments can then be selected which have a length such that essentially all pulp material can be anatomically cleaned from the operative middle portion of a root canal without significantly removing pulp material from the apical root portion.

Operative Middle Portion Phase and Related Sets of Instruments

Tables 1A–1D presented hereinbelow describe the dimensions of four different set of instruments which can be used to clean the operative middle portion in different teeth depending on the particular operative root canal length. These four sets are preferably sold as part of a kit. Although, the kit includes several sets of instruments, only one set of instruments is typically used for cleaning the operative middle portion. The practitioner selects from several sets in the kit depending on the particular length of the operative coronal portion and the operative middle portion. The instruments in Tables 1A–1D are designed to have a working length that is adjustable depending on the placement of a stop such as stop 140 or the position of the handle within the chuck of an endodontic handpiece. Accordingly, the working lengths for the instruments in Tables 1A–1D are respectively 15–18 mm, 19–22 mm, 23–26 mm, and 27–30 mm. The operative middle portion instruments in each set are formed from stainless steel.

TABLE 1A

Operative Middle Portion Instruments (15–18 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 18 mm | 15 mm | 3 mm | 0.10 mm | 0.55 mm | 0.50 mm | 0.025 |
| 10b | 18 mm | 15 mm | 3 mm | 0.13 mm | 0.76 mm | 0.70 mm | 0.035 |
| 10c | 18 mm | 15 mm | 3 mm | 0.13 mm | 1.05 mm | 0.90 mm | 0.051 |
| 10d | 18 mm | 15 mm | 3 mm | 0.13 mm | 1.17 mm | 1.00 mm | 0.058 |

TABLE 1B

Operative Middle Portion Instruments (19–22 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 22 mm | 19 mm | 3 mm | 0.10 mm | 0.65 mm | 0.60 mm | 0.025 |
| 10b | 22 mm | 19 mm | 3 mm | 0.13 mm | 0.90 mm | 0.80 mm | 0.035 |
| 10c | 22 mm | 19 mm | 3 mm | 0.13 mm | 1.14 mm | 1.00 mm | 0.046 |
| 10d | 22 mm | 19 mm | 3 mm | 0.13 mm | 1.45 mm | 1.30 mm | 0.060 |

TABLE 1C

Operative Middle Portion Instruments (23–26 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 26 mm | 23 mm | 3 mm | 0.10 mm | 0.78 mm | 0.70 mm | 0.026 |
| 10b | 26 mm | 23 mm | 3 mm | 0.13 mm | 0.88 mm | 0.80 mm | 0.029 |
| 10c | 26 mm | 23 mm | 3 mm | 0.13 mm | 1.12 mm | 1.00 mm | 0.038 |
| 10d | 26 mm | 23 mm | 3 mm | 0.13 mm | 1.43 mm | 1.30 mm | 0.050 |

TABLE 1D

Operative Middle Portion Instruments (27–30 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 30 mm | 27 mm | 3 mm | 0.10 mm | 0.85 mm | 0.80 mm | 0.025 |
| 10b | 30 mm | 27 mm | 3 mm | 0.13 mm | 1.00 mm | 0.90 mm | 0.029 |
| 10c | 30 mm | 27 mm | 3 mm | 0.13 mm | 1.21 mm | 1.10 mm | 0.036 |
| 10d | 30 mm | 27 mm | 3 mm | 0.13 mm | 1.54 mm | 1.40 mm | 0.047 |

As provided in this example, the instruments having a working length of 19–22 mm as presented in Table 1B are selected for use in a tooth due to the combined length of the operative coronal portion and the operative middle portion of the operative root canal which is in the range of 19–22 mm. More particularly, the root canal of the tooth is slightly longer than about 25 mm so the full 22 mm of the working length is utilized. The set of instruments for cleaning the operative middle portion detailed in Table 1B corresponds with the set of instruments shown in FIG. 1 at 10. Since only one set of instruments is used to clean the operative middle portion only one set is shown in FIG. 1 at 10.

After set 10, as detailed in Table 1B, is selected, the pulp chamber is flooded with an irrigation fluid or filled with a chelating lubricant gel, if the canal is atresic. The instruments in set 10 are then attached to a handpiece to move the instruments in either a rotating or reciprocating motion. These instruments can also be manually moved.

File 10a is first introduced into the operative middle portion followed sequentially by file instrument 10b, 10c and then 10d. Instruments 10a–d are each urged against the root canal for about one minute in conformance with the anatomy of the root canal. More particularly, the instruments are applied to the perimeter of the canal, acting on any protuberances or jagged edges in order to rectify the first two portions, the operative middle portion and the operative coronal portion, while still conforming to the anatomy of the canal.

Note that, as shown in FIG. 1, the diameter at the top of each abrading portion 19a–d is incrementally greater than the diameter of the top of the abrading portion of the preceding file. Accordingly, the diameter of the top end of each successive file introduced into the operative middle portion is greater than the diameter of the top end of each preceding file. This provides for an increased surface area for cleaning the root canal and the ability to more rapidly widen the root canal. The practitioner is able to move the instruments around the perimeter of the operative middle portion of the root canal using the contours of the operative middle portion as a guide for the movement of the instrument such that the original anatomy is enlarged and not significantly altered.

The tip diameter of each file in set of operative middle portion instruments are essentially the same. More particularly, the instruments in each set detailed above has a first instrument 10a with a tip diameter of 0.10 mm while the instruments sequentially used thereafter have a tip diameter of 0.13 mm. Accordingly, the flexibility of the lower half remains essentially constant which is ideal since these portions of the root canal being cleaned tapers from a laminar configuration to a more round shape.

Figure 6B:
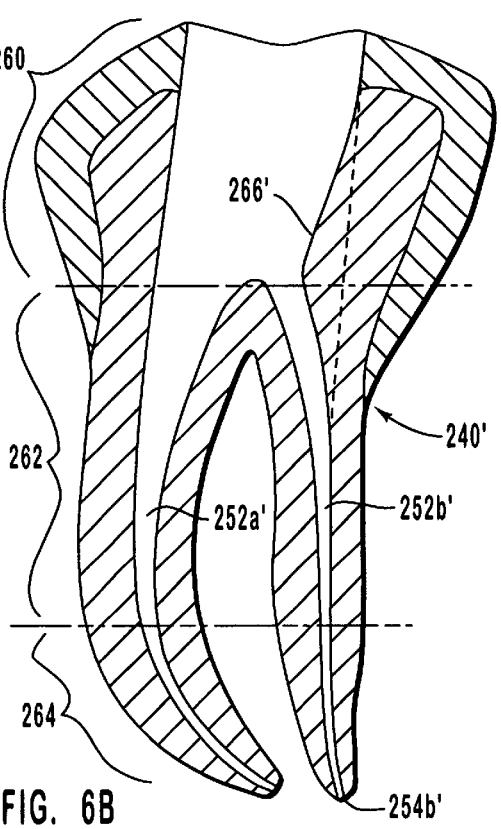
FIG. 6B is a cross-sectional view of the tooth shown in FIG. 6A after rectification and after the operative middle portion has been cleaned.

After cleaning the operative middle portion, the root canal may appear as does root canal 252a' of tooth 240 shown in FIG. 6B. FIG. 6B shows that dentinal shelf 266' has been fully rectified. The other contours of root canal 252a' have been followed to clean operative middle portion 262. As a result, the diameter of the root canal in operative middle portion 262 has been widened, although, the original perimetrical anatomy has not been substantially altered.

Apical Portion Widening Phase and Related Sets of Instruments

A probe is then inserted to the apex of the root canal and another x-ray image is obtained. After the length has been determined the accessibility of the apical portion is assessed. mm. In this example, the set presented in Table 2B is selected since a tooth is being instrumented with a root canal that is slightly longer than about 25 mm. The set presented in Table 2B is shown in FIG. 1 as set 40. Note, however, with the exception of length, the instruments detailed in Table 2A and Table 2C would appear just like set 40. The files of the instruments in the sets detailed in Tables 2A-2C are formed from a suitable material such as nickel titanium or stainless steel.

TABLE 2A

Apical Widening Instruments (21 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 40a | 21 mm | 5 mm | 11 mm | 5 mm | 0.08 mm | 0.28 mm | 0.30 mm | 0.80 mm | 0.04 |
| 40b | 21 mm | 5 mm | 11 mm | 5 mm | 0.08 mm | 0.38 mm | 0.40 mm | 1.1 mm | 0.06 |

TABLE 2B

Apical Widening Instruments (25 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 40a | 25 mm | 5 mm | 15 mm | 5 mm | 0.08 mm | 0.28 mm | 0.30 mm | 0.90 mm | 0.04 |
| 40b | 25 mm | 5 mm | 15 mm | 5 mm | 0.08 mm | 0.38 mm | 0.40 mm | 1.3 mm | 0.06 |

TABLE 2C

Apical Widening Instruments (30 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 40a | 30 mm | 5 mm | 20 mm | 5 mm | 0.08 mm | 0.28 mm | 0.30 mm | 1.1 mm | 0.04 |
| 40b | 30 mm | 5 mm | 20 mm | 5 mm | 0.08 mm | 0.38 mm | 0.40 mm | 1.6 mm | 0.06 |

If the apical portion is initially to small to permit entry of an irrigation cannula then an optional set of instruments is selected for use in improving the access into the apical root portion or stated otherwise to enlarge the constricted region between the operative middle portion and the apical portion. This is achieved by manually moving one or more instruments until the transition zone between the operative middle portion and the apical root portion has been appropriately instrumented to have a diameter of about 0.40 mm, which is suitable for accommodating the diameters of the smallest irrigation needles.

Again the practitioner has a comprehensive kit with several sets of instruments which are designed for improving access into the apical root portion after the pulp material has been removed from the operative middle portion of a root canal. Each set is designed for use in a tooth with a different operative root canal length. Accordingly, only one set from the kit is selected for use in operative root canal based on the length of the particular anatomical root canal being treated.

Tables 2A-2C detail the dimensions of instruments with file lengths which are respectively 21 mm, 25 mm and 30

Each file has three sections including a smooth shank portion, a square portion and an abrading portion. The smooth shank portion enables stops be positioned on the file to adjust the working length of the file. Each smooth shank portion of each file has a length of about 5 mm with various diameters. The instruments can be used for all operative lengths that are likely to be encountered in clinical practice through the positioning of the stops at the predetermined lengths. While the instruments can be offered in a more expanded series of millimetrically different lengths, the use of stops is acceptable, particularly since, these instruments are manually moved.

In each set, the diameter at the top of the square portion of instrument number 40a and instrument number 40b is respectively 0.30 mm and 0.40 mm. The abrading portion is formed by twisting the square section so that the abrading portion has a K-file configuration. The instruments in each set all have the same tip diameters. The taper of the files from the tip ($D_1$) to the diameter at the top of the square portion ($D_3$) remains constant and is respectively 0.04 and 0.06 for instrument number 40a and instrument number 40b in each set.

Preferably, instrument 40a is first utilized and then instrument 40b to obtain, in a gradual manner, the desired enlargement of the specific transition zone between the operative middle portion and the apical portion. This enlargement is also preferably achieved without significantly changing the diameter of the apical portion of the canal. Accordingly, the tip diameter ($D_1$) of the various instruments in this set remains constant while the diameter at the top of the cutting area or abrading portion ($D_2$), located 5 mm from the tip, is graduated from one instrument to the next, reaching a maximum diameter of 0.38 mm. The rest of the shaft, up to the handle, does not have a cutting surface. To the extent that these instruments are used to expand the apical portion of the canal, the practitioner should constantly bear in mind the average diameters of the canals and the average thicknesses of the parietal walls at the apex.

Figure 6C:
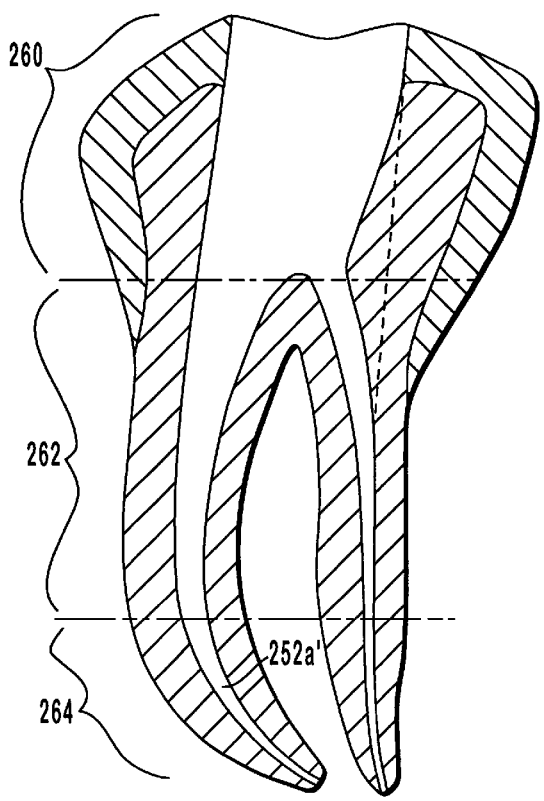
FIG. 6C is a cross-sectional view of the tooth shown in FIG. 6A after the apical portion has been widened.

After widening the apical portion of the root canal with the set shown at 40 in FIG. 1 and as detailed in Table 2B, the root canal may appear as does root canal 252a' in FIG. 6C with a widened transition into apical portion 264. More particularly, the region of root canal 252a' extending from the bottom of operative middle portion 262 to the top half of apical portion 264 has been noticeably widened. The bottom half of apical portion 264 has also been widened but to a much lesser degree.

Apical Portion Cleaning Phase and Related Sets of Instruments

After the access into the apical portion has been adequately widened as discussed hereinabove and as shown in FIG. 6C, the apical portion is cleaned. Cleaning is halted as the working length is determined by the operator. The practitioner should determine this length beforehand, based on the biological condition of the apico-periapical region, in terms of typical morphometrics of the diameters and thicknesses at the apex, and in accordance with the amount of widening to be applied to the apical portion of the canal.

Again sets of instruments are provided with each set having a different length. Three sets of instruments are described hereinbelow which are designed for removing and cleaning essentially all pulp material from the apical root portion after access into the apical root portion has been improved by a set of instruments such as set 40 detailed in Table 2B. In some instances, the instruments described in this example can also be used to clean the pulp material from the root canal immediately after the operative middle portion has been cleaned by a set of instruments such as the sets presented in Table 1B. P Tables 3A-3C detail the dimensions of instruments with file lengths which are respectively 21 mm, 25 mm and 30 mm. However, please note that only instruments from set detailed in Table 3B are used in the tooth being cleaned in this example as the files in this set having the appropriate length. Instruments 70a–l in the set presented in Table 3B respectively correspond with instruments 70a–l of set 70 shown in FIG. 1. The instruments in set 70 have a similar appearance as the instruments in set 40. The sets of instruments presented in Table 3A and 3C have a similar appearance to instruments detailed in Table 3B and shown at 70, however, the files have different lengths. In addition to the lengths and diameters of the various portions, the taper of each file from the tip ($D_1$) to the diameter at the top of the square portion ($D_3$) is provided in each table.

TABLE 3A

Apical Cleaning Instruments (21 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 70a | 21 mm | 5 mm | 11 mm | 5 mm | 0.10 mm | 0.20 mm | 0.42 mm | 0.50 mm | 0.02 |
| 70b | 21 mm | 5 mm | 11 mm | 5 mm | 0.15 mm | 0.25 mm | 0.47 mm | 0.50 mm | 0.02 |
| 70c | 21 mm | 5 mm | 11 mm | 5 mm | 0.20 mm | 0.30 mm | 0.52 mm | 0.60 mm | 0.02 |
| 70d | 21 mm | 5 mm | 11 mm | 5 mm | 0.25 mm | 0.375 mm | 0.65 mm | 0.70 mm | 0.025 |
| 70e | 21 mm | 5 mm | 11 mm | 5 mm | 0.30 mm | 0.425 mm | 0.70 mm | 0.70 mm | 0.025 |
| 70f | 21 mm | 5 mm | 11 mm | 5 mm | 0.35 mm | 0.475 mm | 0.75 mm | 0.80 mm | 0.025 |
| 70g | 21 mm | 5 mm | 11 mm | 5 mm | 0.40 mm | 0.525 mm | 0.80 mm | 0.80 mm | 0.025 |
| 70h | 21 mm | 5 mm | 11 mm | 5 mm | 0.50 mm | 0.625 mm | 0.90 mm | 0.90 mm | 0.025 |
| 70i | 21 mm | 5 mm | 11 mm | 5 mm | 0.60 mm | 0.725 mm | 1.0 mm | 1.0 mm | 0.025 |
| 70j | 21 mm | 5 mm | 11 mm | 5 mm | 0.70 mm | 0.825 mm | 1.1 mm | 1.1 mm | 0.025 |
| 70k | 21 mm | 5 mm | 11 mm | 5 mm | 0.80 mm | 0.925 mm | 1.2 mm | 1.2 mm | 0.025 |
| 70l | 21 mm | 5 mm | 11 mm | 5 mm | 1.0 mm | 1.125 mm | 1.4 mm | 1.5 mm | 0.025 |

TABLE 3B

Apical Cleaning Instruments (25 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 70a | 25 mm | 5 mm | 15 mm | 5 mm | 0.10 mm | 0.20 mm | 0.50 mm | 0.50 mm | 0.02 |
| 70b | 25 mm | 5 mm | 15 mm | 5 mm | 0.15 mm | 0.25 mm | 0.55 mm | 0.60 mm | 0.02 |
| 70c | 25 mm | 5 mm | 15 mm | 5 mm | 0.20 mm | 0.30 mm | 0.60 mm | 0.60 mm | 0.02 |
| 70d | 25 mm | 5 mm | 15 mm | 5 mm | 0.25 mm | 0.375 mm | 0.75 mm | 0.80 mm | 0.025 |
| 70e | 25 mm | 5 mm | 15 mm | 5 mm | 0.30 mm | 0.425 mm | 0.80 mm | 0.80 mm | 0.025 |
| 70f | 25 mm | 5 mm | 15 mm | 5 mm | 0.35 mm | 0.475 mm | 0.85 mm | 0.90 mm | 0.025 |
| 70g | 25 mm | 5 mm | 15 mm | 5 mm | 0.40 mm | 0.525 mm | 0.90 mm | 0.90 mm | 0.025 |

TABLE 3B-continued

Apical Cleaning Instruments (25 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 70h | 25 mm | 5 mm | 15 mm | 5 mm | 0.50 mm | 0.625 mm | 1.0 mm | 1.0 mm | 0.025 |
| 70i | 25 mm | 5 mm | 15 mm | 5 mm | 0.60 mm | 0.725 mm | 1.1 mm | 1.1 mm | 0.025 |
| 70j | 25 mm | 5 mm | 15 mm | 5 mm | 0.70 mm | 0.825 mm | 1.2 mm | 1.2 mm | 0.025 |
| 70k | 25 mm | 5 mm | 15 mm | 5 mm | 0.80 mm | 0.925 mm | 1.3 mm | 1.3 mm | 0.025 |
| 70l | 25 mm | 5 mm | 15 mm | 5 mm | 1.0 mm | 1.125 mm | 1.5 mm | 1.5 mm | 0.025 |

TABLE 3C

Apical Cleaning Instruments (30 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 70a | 30 mm | 5 mm | 20 mm | 5 mm | 0.10 mm | .20 mm | 0.60 mm | 0.60 mm | 0.02 |
| 70b | 30 mm | 5 mm | 20 mm | 5 mm | 0.15 mm | 0.25 mm | 0.65 mm | 0.70 mm | 0.02 |
| 70c | 30 mm | 5 mm | 20 mm | 5 mm | 0.20 mm | 0.30 mm | 0.70 mm | 0.70 mm | 0.02 |
| 70d | 30 mm | 5 mm | 20 mm | 5 mm | 0.25 mm | 0.375 mm | 0.875 mm | 0.90 mm | 0.025 |
| 70e | 30 mm | 5 mm | 20 mm | 5 mm | 0.30 mm | 0.425 mm | 0.925 mm | 1.0 mm | 0.025 |
| 70f | 30 mm | 5 mm | 20 mm | 5 mm | 0.35 mm | 0.475 mm | 0.975 mm | 1.0 mm | 0.025 |
| 70g | 30 mm | 5 mm | 20 mm | 5 mm | 0.40 mm | 0.525 mm | 1.025 mm | 1.1 mm | 0.025 |
| 70h | 30 mm | 5 mm | 20 mm | 5 mm | 0.50 mm | 0.625 mm | 1.125 mm | 1.2 mm | 0.025 |
| 70i | 30 mm | 5 mm | 20 mm | 5 mm | 0.60 mm | 0.725 mm | 1.225 mm | 1.3 mm | 0.025 |
| 70j | 30 mm | 5 mm | 20 mm | 5 mm | 0.70 mm | 0.825 mm | 1.325 mm | 1.4 mm | 0.025 |
| 70k | 30 mm | 5 mm | 20 mm | 5 mm | 0.80 mm | 0.925 mm | 1.425 mm | 1.5 mm | 0.025 |
| 70l | 30 mm | 5 mm | 20 mm | 5 mm | 1.0 mm | 1.125 mm | 1.625 mm | 1.7 mm | 0.025 |

To ensure that the files have an appropriate working length, it may be necessary to place stops around the shank portions of the files identified for example at 76. The practitioner then selects an instrument from set 70 shown in FIG. 1 and detailed in Table 3B. After selecting an instrument, the practitioner then determines, based on feel and experience, whether the file is appropriately sized or whether a larger or smaller file is needed. For instance, if the practitioner selects instrument number 70b which has a tip diameter of 0.15 mm and the file binds after insertion, then the practitioner would switch to instrument number 70a which has a tip diameter of 0.10 mm. Similarly, if instrument number 70b is too loose then the practitioner would then switch to instrument number 70c which has a tip diameter of 0.20 mm. The practitioner then uses that appropriately sized instrument to clean the apical portion of the root canal by hand. If the practitioner concludes after using an appropriately sized file, that further instrumentation is still needed within the apical portion then the instrument with the next largest file may be used. It is typically unnecessary to use a third instrument with an even larger file after using a series of two instruments. However, the practitioner may clean the apical root portion with a series of more than two instruments as deemed necessary by the practitioner in order to fully clean the apical portion. This procedure is preferably followed until an instrument has been used that has an abrading portion with a taper that is greater than 0.20 such as instrument 70d. Abrading portion 79d of file 74d has a taper that is 0.025. If file 74d is the first file inserted into the root canal then it may be necessary to utilize one or more files with larger tip diameters that also have abrading portions with a taper of 0.025.

Figure 6D:
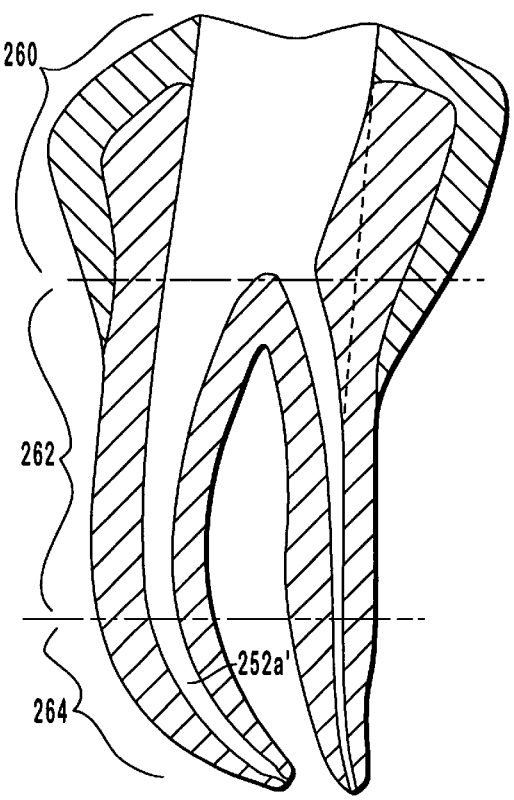
FIG. 6D is a cross-sectional view of the tooth shown in FIG. 6A after the apical portion has been cleaned.

After the apical portion of the root canal has been cleaned with the set shown at 70 in FIG. 1 and as detailed in Table 3B, the root canal may appear as does root canal 252a' shown in FIG. 6D with a cleaned apical portion 264. More particularly, after use of an instrument or instruments, apical portion 264 may appear as shown in FIG. 6D. Note that cleaning apical portion 264 has substantially widened the bottom half of apical portion 264 while the top half is less significantly flared when compared to its appearance before being cleaned. The appearance of apical portion 264 results from the use of increasingly larger abrading portions to widen and to clean the apical portion.

Set 10 and set 40 are preferably disposed after use. However, since only one or two instruments from set 70 are used, it is preferable to replace or clean the instruments used from set 70. All of the sets of instruments described in this example may be sold together as a comprehensive kit or various sets may be grouped together as kits intended for use with teeth of particular lengths. For example, the sets used in the tooth cleaned in this example which are detailed in Table 1B, 2B and 3B may be sold together. Additionally, since set 10 and set 40 are intended to be single use sets these sets may also be sold together as a single use disposable kit.

Example 2

This example describes an exemplary system for cleaning a root canal without abrasively cleaning the apical portion. The apical portion is cleaned after the operative middle portion has been cleaned with set 10 as set forth in Example 1. Access into the apical portion has been improved through the use of set 40 as described in Example 1. Cleaning of the apical portion is then initiated by inserting a cleaning instrument into the apical portion as shown in FIGS. 5A–5B and delivering irrigants. The cleaning instrument is a cannula 360 of an endodontic irrigator tip 320, as previously described in reference to FIGS. 5A–5B. After syringe 390 has been used to deliver irrigants into root canal 254b, the irrigants and any remaining debris are removed by aspiration via irrigator tip 320 coupled to an aspirator.

Note in addition to set 10 and set 40 being disposable after use, irrigator tip 320 is also preferably disposable. Note also that instead of a large set of instruments like set 70, only a single irrigator tip need be used so it is much less expensive to merely irrigate. It is also less time intensive since it is not necessary to use a series of apical instruments. All of the instruments described in this example may be sold individually or together as a comprehensive kit.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for cleaning the operative coronal portion and the operative middle portion of an operative root canal of a tooth, the method comprising:

exposing the root canal by removing a portion of the tooth at a crown thereof and by removing the top of the pulp chamber;

obtaining a set of first endodontic instruments wherein each instrument has a file with an abrading portion for removing pulp material, each file having a length corresponding to at least the combined length of the operative coronal portion and the operative middle portion;

removing and cleaning essentially all pulp material from the operative coronal portion and the operative middle portion by sequentially introducing the files of the instruments in the set of first endodontic instruments into the operative middle portion and then flexing each file such that the abrading portion of each file is urged against root canal surfaces within the operative middle portion as each instrument is rotated and moved in a cleaning motion in conformance with the anatomical shape of the operative middle portion by following the contours of the operative middle portion as a guide for movement of each instrument, and without significantly extending the file of each instrument into the apical root portion, wherein each sequentially introduced file has greater rigidity than the previously introduced file along at least an upper part of the abrading portion of each file to enable each sequentially introduced file to more rapidly and aggressively clean than the previously introduced file.

2. A method as defined in claim 1, wherein following the contours of the operative middle portion involves moving each instrument around the perimeter of the operative middle portion of the operative root canal.

3. A method as defined in claim 1, wherein following the contours of the operative middle portion involves moving each instrument along a side of the operative middle portion of the operative root canal such that each instrument generally has more than one center of motion during the step of removing and cleaning essentially all pulp material from the operative middle portion.

4. A method as defined in claim 1, wherein each file of each instrument in the set of first endodontic instruments comprises has a tip opposite a top end, and wherein the files of all of the instruments in the set of first endodontic instruments have essentially the same tip diameter while having distinct top end diameters to enable the files to be sequentially introduced into the operative middle portion such that each successive file has a greater top end diameter than that of the preceding file.

5. A method as defined in claim 1, wherein each file of each instrument in the set of first endodontic instruments has a tip opposite a top end, and wherein the files of all of the instruments in the set of first endodontic instruments have distinct tapers to enable the files to be sequentially introduced into the operative middle portion such that each successive file has a greater taper than that of the preceding file.

6. A method as defined in claim 1, wherein the file of each instrument in the set of first endodontic instruments extends from a handle.

7. A method as defined in claim 1, further comprising the step of determining the working length of the operative root canal to select an appropriate instrument for removing and cleaning essentially all pulp material from the operative coronal portion and the operative middle portion.

8. A method as defined in claim 1, further comprising the step of positioning at least one stop on the file of each instrument in the set of first endodontic instruments sequentially introduced into the operative middle portion.

9. A method as defined in claim 1, further comprising the step of minimizing obstructions in the operative root canal before removing and cleaning essentially all pulp material from the operative middle portion such that instruments can be inserted in the operative middle portion in a relatively straight manner.

10. A method for anatomical cleaning of the operative coronal portion and the operative middle portion of an operative root canal in a tooth, the method comprising:

exposing the root canal by removing a portion of the tooth at a crown thereof and by removing the top of the pulp chamber;

obtaining a set of first endodontic instruments wherein each instrument has a file that extends from an end means for grasping and operatively moving the file, wherein the file has an abrading portion for removing pulp material that extends from a tip to a top end of the abrading portion, and wherein each file has a length corresponding to at least the combined length of the operative coronal portion and the operative middle portion;

removing and cleaning essentially all pulp material from the operative coronal portion and the operative middle portion by sequentially introducing the files of the instruments in the set of first endodontic instruments into the operative middle portion such that each successive file has an abrading portion with a greater top end diameter than that of the preceding file, and then flexing each file such that the abrading portion of each file is urged against root canal surfaces within the operative middle portion as each instrument is rotated and moved in a cleaning motion in conformance with the anatomical shape of the operative middle portion by following the contours of the operative middle portion as a guide for movement of each instrument, without significantly extending the file of each instrument into the apical root portion, and wherein at least the top end of each abrading portion of each sequentially introduced file applies greater force against the root canal surfaces than the previously introduced file to enable each sequentially introduced file to more rapidly and aggressively clean than the previously introduced file.

11. A method as defined in claim 10, wherein following the contours of the operative middle portion involves moving each instrument around the perimeter of the operative middle portion of the operative root canal.

12. A method as defined in claim 10, wherein following the contours of the operative middle portion involves moving each instrument along a side of the operative middle portion of the operative root canal such that each instrument generally has more than one center of motion during the step of removing and cleaning essentially all pulp material from the operative middle portion.

13. A method as defined in claim 10, wherein the files of all of the instruments in the set of first endodontic instruments have essentially the same tip diameter.

14. A method as defined in claim 10, wherein the end means for grasping and operatively moving the file is a handle.

15. A method as defined in claim 10, further comprising the step of determining the working length of the operative root canal to select an appropriate instrument for removing and cleaning essentially all pulp material from the operative coronal portion and the operative middle portion.

16. A method as defined in claim 10, further comprising the step of positioning at least one stop on the file of each instrument in the set of first endodontic instruments sequentially introduced into the operative middle portion.

17. A method as defined in claim 10, further comprising the step of minimizing obstructions in the operative root canal before removing and cleaning essentially all pulp material from the operative middle portion such that instruments can be inserted in the operative middle portion in a relatively straight manner.

18. An endodontic instrument system adapted for anatomical cleaning of the operative coronal portion and the operative middle portion of an operative root canal in a tooth, the endodontic instrument system comprising:

a set of first endodontic instruments configured for sequential use in the operative middle portion of an operative root canal to anatomically clean essentially all pulp material from the operative middle portion without significantly extending into the apical root portion, each instrument in the set including a file having a length corresponding to at least the combined length of the operative coronal portion and the operative middle portion in order to remove pulp material from essentially all of the operative middle portion of the operative root canal, the file having an abrading portion adapted for removing pulp material through abrasive action as the file is rotated, the abrading portion being located on the file and extending between a tip to a top end along at least most of the file, the file being able to flex such that the abrading portion is urged against root canal surfaces while the file is rotated and moved in a cleaning motion, thereby enabling contours of the operative middle portion to be used as a guide for movement of the file in conformance to the anatomical shape of the operative middle portion while effecting removal and cleaning of pulp material from essentially all of the operative middle portion, wherein the file of each instrument in the set of first endodontic instruments has sufficient rigidity to apply pressure against the root canal surfaces via the abrading portion as each file is flexed to urge the abrading portion against root canal surfaces and as each file is simultaneously moved in a cleaning motion, and wherein each sequentially introduced file has greater rigidity than the previously introduced file along at least an upper part of the abrading portion of each file to enable each sequentially introduced file to more rapidly and aggressively clean than the previously introduced file, and a handle connected to each file opposite from the tip, the handle being configured to enable a user to operatively move the file in an abrasive action while bending and flexing the file within the operative middle portion of the operative root canal.

19. An endodontic instrument system as defined in claim 18, wherein the file of each instrument in the set of first endodontic instruments has adequate resilience to avoid being substantially deformed as each file is flexed to urge the abrading portion against root canal surfaces and as each file is simultaneously moved in a cleaning motion.

20. An endodontic instrument system as defined in claim 18, wherein the file of each instrument in the set of first endodontic instruments is configured to enable a practitioner to move the file around the perimeter of the operative middle portion of the operative root canal.

21. An endodontic instrument system as defined in claim 18, wherein the file of each instrument in the set of first endodontic instruments is configured to enable a practitioner to move the file along a side of the operative middle portion in a manner such that the tip does not remain primarily in one position as the operative middle portion is cleaned.

22. An endodontic instrument system as defined in claim 18, wherein the file of each instrument in the set of first endodontic instruments has essentially the same length.

23. An endodontic instrument system as defined in claim 18, wherein the files of all of the instruments in the set of first endodontic instruments have essentially the same tip diameter while the abrading portions have distinct top end diameters to enable the files to be sequentially introduced into the operative middle portion such that each successive file has an abrading portion with a greater top end diameter than that of the preceding file.

24. An endodontic instrument system as defined in claim 18, wherein the abrading portions of the files of all of the instruments in the set of first endodontic instruments have distinct tapers to enable the files to be sequentially introduced into the operative middle portion such that each successive file has an abrading portion with a greater taper than that of the preceding file.

25. An endodontic instrument system as defined in claim 18, further comprising a stop configured to be positioned on one of the files of the first endodontic instruments in order to limit insertion of the file into the operative coronal portion and the operative middle portion without substantially extending into the apical portion.

26. An endodontic instrument system adapted for anatomical cleaning of the operative coronal portion and the operative middle portion of an operative root canal in a tooth, the endodontic instrument system comprising:

a set of first endodontic instruments configured for sequential use in the operative middle portion of an operative root canal to anatomically clean essentially all pulp material from the operative middle portion without significantly extending into the apical root portion, each instrument in the set including a file having a length corresponding to at least the combined length of the operative coronal portion and the operative middle portion in order to remove pulp material from essentially all of the operative middle portion of the operative root canal, the file having an abrading portion adapted for removing pulp material through abrasive action as the file is rotated, the abrading portion being located on the file and extending from a tip to a top end along at least most of the file, the file being able to flex such that the abrading portion is urged against root canal surfaces while the file is rotated and moved in a cleaning motion, thereby enabling contours of the operative middle portion to be used as a guide for movement of the file in conformance to the anatomical shape of the operative middle portion while effecting removal and cleaning of pulp material from essentially all of the operative middle portion, wherein the files of all of the instruments in the set of first endodontic instruments have the same length and essentially the same tip diameter while the abrading portions have distinct top end diameters to enable the files to be sequentially introduced into the operative middle portion such that each successive file has an abrading portion with a greater top end diameter than that of the preceding file, and wherein each sequentially introduced file has greater rigidity than the previously introduced file along at least an upper part of the abrading portion of each file to enable each sequentially introduced file to more rapidly and aggressively clean than the previously introduced file, and a handle connected to the top end of the file such that movement of the handle also moves at least the top end of the file along a common axis with the handle, the handle being configured to enable a user to operatively move the file in an abrasive action while flexing the file within the operative middle portion of the operative root canal.

* * * * *

UNITED STATES PATENT AND TRADEMARK OFFICE
CERTIFICATE OF CORRECTION

PATENT NO. : 6,558,163 B2
DATED : May 6, 2003
INVENTOR(S) : Francesco Riitano

It is certified that error appears in the above-identified patent and that said Letters Patent is hereby corrected as shown below:

Column 2,
Line 17, after "thereof" insert -- . --
Line 49, after "cleaned" insert -- . --

Column 4,
Line 3, change "it" to -- is --
Line 9, delete "an"

Column 5,
Line 2, delete "then the root canal"
Line 3, after "areas" delete "and"
Line 6, delete "a"
Line 34, after "and" insert -- cleaning --
Line 62, delete "was"
Line 63, change "weaken" to -- weakening --.

Column 6,
Line 6, after "problem" insert -- . --

Column 10,
Line 19, after "located" insert -- . --

Column 13,
Line 3, delete "is"
Line 16, before "the" delete "to clean"

Column 15,
Line 45, after "portion" insert -- . --
Line 45, start a new paragraph with "The"

Column 20,
Line 65, change "includes" to -- include --

Column 22,
Line 30, change "Endo-Eze(®)" to -- Endo-Eze® --

Column 23,
Line 35, change "File-Ezet" to -- File-Eze® --

Column 24,
Line 59, change "6 mm" to -- 6 mm. --

UNITED STATES PATENT AND TRADEMARK OFFICE
CERTIFICATE OF CORRECTION

PATENT NO. : 6,558,163 B2
DATED : May 6, 2003
INVENTOR(S) : Francesco Riitano

It is certified that error appears in the above-identified patent and that said Letters Patent is hereby corrected as shown below:

Column 26,
Line 16, after "random" insert -- . --
Line 41, change "then" to -- the --

Column 28,
Line 44, after "thereof" insert -- . --

Column 30,
Line 35, change "set" to -- sets --

Column 36,
Line 17, delete "P"
Line 17, start a new paragraph with "Tables 3A-3C"
Line 20, after "from" insert -- the --
Line 24, start a new paragraph with "The"

Column 39,
Line 16, change "illustrated" to -- illustrative --

Column 40,
Line 1, delete "has"

Signed and Sealed this

Twenty-fourth Day of February, 2004

JON W. DUDAS
*Acting Director of the United States Patent and Trademark Office*